US007732134B2

(12) United States Patent
Kudaravalli et al.

(10) Patent No.: US 7,732,134 B2
(45) Date of Patent: Jun. 8, 2010

(54) METHODS TO PREDICT CHOLESTEROL ELEVATION DURING IMMUNOSUPPRESSANT THERAPY

(75) Inventors: Sridhar Kudaravalli, Chicago, IL (US); Mihael Hristos Polymeropoulos, Potomac, MD (US); Rosarelis Torres, Bethesda, MD (US); Curt Douglas Wolfgang, Germantown, MD (US)

(73) Assignee: Novartis AG, Basel (CH)

( * ) Notice: Subject to any disclaimer, the term of this patent is extended or adjusted under 35 U.S.C. 154(b) by 788 days.

(21) Appl. No.: 10/529,613

(22) PCT Filed: Sep. 29, 2003

(86) PCT No.: PCT/EP03/10798

§ 371 (c)(1),
(2), (4) Date: Jun. 8, 2005

(87) PCT Pub. No.: WO2004/029618

PCT Pub. Date: Apr. 8, 2004

(65) Prior Publication Data

US 2006/0246439 A1 Nov. 2, 2006

Related U.S. Application Data

(60) Provisional application No. 60/415,123, filed on Sep. 30, 2002.

(51) Int. Cl.
*C12Q 1/68* (2006.01)
*C07H 21/04* (2006.01)
*C12P 19/34* (2006.01)

(52) U.S. Cl. .......................... 435/6; 536/24.3; 435/91.2

(58) Field of Classification Search ....................... None
See application file for complete search history.

(56) References Cited

U.S. PATENT DOCUMENTS 6,268,142 B1 * 7/2001 Duff et al. ..................... 435/6
2003/0235890 A1 * 12/2003 Wyllie et al. ............. 435/69.52

FOREIGN PATENT DOCUMENTS

WO 00/72015 11/2000

WO 97/06180 2/2002

OTHER PUBLICATIONS

Pediatia Polska (2004) vol. 79, pp. 127-134).*
Brenner et al (Trends in Genetics (2001) vol. 17, pp. 414-418).*
Moore (Drug Safety (2001) vol. 24, pp. 755-766).*
Hirschhorn et al. (Genetics in Medicine. vol. 4, No. 2, pp. 45-61, Mar. 2002).*
Genecard (GC02M113303, Apr. 18, 2008, pp. 1-15).*
El Omar (Nature (2000) vol. 404, pp. 398-402).*
Matzkies (Transplantation proceedings (2002) vol. 34, pp. 1795-1796).*
El-Omar, et al., "Interleukin-1 polymorphisms associated with increased risk of gastric cancer", Nature, vol. 404 (2000).
Mattila, et al., "Association of an interleukin 1B gene polymorphism (-511) with Parkinson's disease in Finnish patients", J. of Med. Genetics (2002).
Kerschdorfer, et al., "Lipoprotein(a) plasma concentration after renal transplantation: a prospective evaluation after 4 years of follow-up", Atherosclerosis, vol. 144 (1999).
Database EMBL Online: Clark, et al., "Human gene for prointerleukin 1 beta", Accession No. X04500-XP002276413 (1997).
Radeau, et al., "HDL cholesterol and TaqIB cholesteryl ester transfer protein gene polymorphism in renal transplant recipients", Nephron, vol. 84 (2000).
Blum, Conrad B., "Effects of Sirolimus on Lipids in Renal Allograft Recipients: An Analysis Using the Framingham Risk Model", American Journal of Transplantation, vol. 2, pp. 551-559, (2002).
El-Omar et al., "Interleukin-1 Polymorphisms Associated with Increased Risk of Gastric Cancer", Nature, vol. 404, pp. 398-402, (2000).
Morrisett et al., "Effects of Sirolimus on Plasma Lipids, Lipoprotein Levels, and Fatty Acid Metabolism in Renal Transplant Patients" Journal of Lipid Research, vol. 43, pp. 1170-1180, (2002).
Radeau, T. et al., "HDL Cholesterol and Taq1B Cholesteryl Ester Transfer Protein Gene Polymorphism in Renal Transplant Recipients", Nephron, vol. 84, pp. 333-341, (2000).
Van Darnme-Lornbaerts, R., "Single dose pharmacokinetics and tolerability of everolimus in stable pediatric renal transplant patients", Pediatric Transplantation, vol. 6, No. 2, pp. 147-152 (2002).
"Thrombosis and Circulation", vol. 7, No. 2, pp. 164-168 (1999) and translation of Summary p. 164.
Official Action issued Jun. 12, 2009, in corresponding Japanese Patent Application 2004-539048.

* cited by examiner

*Primary Examiner*—Steven C Pohnert
(74) *Attorney, Agent, or Firm*—Leslie Fischer

(57) ABSTRACT

This invention provides methods to predict the degree of elevation of serum cholesterol levels in patients treated with immunosuppressive medication. This invention also provides treatment strategies based on these predictions and kits to carry out these methods.

3 Claims, 7 Drawing Sheets

Figure 1. LS Mean Total Cholesterol Levels Compared to the (-511) IL-1β CC, CT or TT Genotypes In All Treatment Groups Combined Within the RAD B251 Clinical Trial Figure 2. LS Mean Total Cholesterol Levels Compared to the (-31) IL-1β CC, CT or TT Genotypes In All Treatment Groups Combined Within the RAD B251 Clinical Trial Figure 3. LS Mean HDL Cholesterol Levels Compared to the (-511) IL-1β CC, CT or TT Genotypes In All Treatment Groups Combined Within the RAD B251 Clinical Trial Figure 4. LS Mean HDL Cholesterol Levels Compared to the (-31) IL-1β CC, CT or TT Genotypes In All Treatment Groups Combined Within the RAD B251 Clinical Trial Figure 5. LS Mean LDL Cholesterol Levels Compared to the (-511) IL-1β CC, CT or TT Genotypes In All Treatment Groups Within the RAD B251 Clinical Trial Figure 6. LS Mean LDL Cholesterol Levels Compared to the (-31) IL-1β CC, CT or TT Genotypes In All Treatments Groups Within the RAD B251 Clinical Trial

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: IL-1 (-511) - forward primer

<400> SEQUENCE: 1
gcagagctca tctggcattg                                                     20

<210> SEQ ID NO 2
<211> LENGTH: 20
<212> TYPE: DNA
<213> ORGANISM: Artificial
<220> FEATURE:
<223> OTHER INFORMATION: IL-1 (-511) -reverse primer

<400> SEQUENCE: 2
tatgtgggac aaagtggaag                                                     20

<210> SEQ ID NO 3
<211> LENGTH: 22
<212> TYPE: DNA
<213> ORGANISM: Artificial
<220> FEATURE:
<223> OTHER INFORMATION: IL-1  (-31) -forward primer

<400> SEQUENCE: 3
gcacaacgat tgtcaggaaa ac                                                  22

<210> SEQ ID NO 4
<211> LENGTH: 22
<212> TYPE: DNA
<213> ORGANISM: Artificial
<220> FEATURE:
<223> OTHER INFORMATION: IL-1  (-31) -reverse primer

<400> SEQUENCE: 4
atgcatacac acaaagaggc ag                                                  22

<210> SEQ ID NO 5
<211> LENGTH: 55
<212> TYPE: DNA
<213> ORGANISM: Homo sapiens
<220> FEATURE:
<221> NAME/KEY: misc_feature
<222> LOCATION: (1)..(55)
<223> OTHER INFORMATION: Nucleotide sequence surrounding the (-511) IL-1
      polymorphism, allele 1
```

```
<220> FEATURE:
<221> NAME/KEY: allele
<222> LOCATION: (1)..(55)
<223> OTHER INFORMATION: Nucleotide sequence surrounding the (-511) IL-1
      polymorphism, allele 1

<400> SEQUENCE: 5
ctgcaattga cagagagctc ccgaggcaga gaacagcacc caaggtagag accca          55

<210> SEQ ID NO 6
<211> LENGTH: 55
<212> TYPE: DNA
<213> ORGANISM: Homo sapiens
<220> FEATURE:
<221> NAME/KEY: allele
<222> LOCATION: (1)..(55)
<223> OTHER INFORMATION: Nucleotide sequence surrounding the (-511) IL-1
      polymorhism, allele 2

<400> SEQUENCE: 6
ctgcaattga cagagagctc ctgaggcaga gaacagcacc caaggtagag accca          55

<210> SEQ ID NO 7
<211> LENGTH: 63
<212> TYPE: DNA
<213> ORGANISM: Homo sapiens
<220> FEATURE:
<221> NAME/KEY: allele
<222> LOCATION: (1)..(63)
<223> OTHER INFORMATION: Nucleotide sequence surrounding the (-31) IL-1
      polymorhism, allele 1

<400> SEQUENCE: 7
tcctacttct gcttttgaaa gccataaaaa cagcgaggga gaaactggca gataccaaac     60
ctc                                                                  63

<210> SEQ ID NO 8
<211> LENGTH: 63
<212> TYPE: DNA
<213> ORGANISM: Homo sapiens
<220> FEATURE:
<221> NAME/KEY: allele
<222> LOCATION: (1)..(63)
<223> OTHER INFORMATION: Nucleotidee sequence surrounding the (-31) IL-1
      polymorhism, allele 2

<400> SEQUENCE: 8
tcctacttct gcttttgaaa gctataaaaa cagcgaggga gaaactggca gataccaaac     60
ctc                                                                  63

<210> SEQ ID NO 9
<211> LENGTH: 55
<212> TYPE: DNA
<213> ORGANISM: Homo sapiens
<220> FEATURE:
<221> NAME/KEY: allele
<222> LOCATION: (1)..(55)
<223> OTHER INFORMATION: Nucleotide sequence surrounding the (-511) IL-1
      polymorphism;
<220> FEATURE:
<221> NAME/KEY: misc_feature
<222> LOCATION: (22)..(22)
<223> OTHER INFORMATION: n at position 22 may be c or t

<400> SEQUENCE: 9
ctgcaattga cagagagctc cngaggcaga gaacagcacc caaggtagag accca          55
```

<210> SEQ ID NO 10
<211> LENGTH: 63
<212> TYPE: DNA
<213> ORGANISM: Homo sapiens
<220> FEATURE:
<221> NAME/KEY: allele
<222> LOCATION: (1)..(63)
<223> OTHER INFORMATION: Nucleotide sequence surrounding teh (-31) IL-1 polymorphism
<220> FEATURE:
<221> NAME/KEY: misc_feature
<222> LOCATION: (23)..(23)
<223> OTHER INFORMATION: n at position 23 may be c or t

<400> SEQUENCE: 10

```
tcctacttct gcttttgaaa gcnataaaaa cagcgaggga gaaactggca gataccaaac      60
ctc                                                                   63
```

<210> SEQ ID NO 11
<211> LENGTH: 9721
<212> TYPE: DNA
<213> ORGANISM: Homo sapiens
<220> FEATURE:
<221> NAME/KEY: misc_feature
<222> LOCATION: (135)..(135)
<223> OTHER INFORMATION: n at position 135 may be c or t
<220> FEATURE:
<221> NAME/KEY: misc_feature
<222> LOCATION: (136)..(136)
<223> OTHER INFORMATION: n at positiion 136 may be c or t

<400> SEQUENCE: 11

```
agaaagaaag agagagagaa agaaaagaaa gaggaaggaa ggaaggaagg aagaaagaca      60
ggctctgagg aaggtggcag ttcctacaac gggagaacca gtggttaatt tgcaaagtgg     120
atcctgtgga ggcanncaga ggagtcccct aggccaccca gacagggctt ttagctatct     180
gcaggccaga caccaaattt caggagggct cagtgttagg aatggattat ggcttatcaa     240
attcacagga aactaacatg ttgaacagct tttagatttc ctgtggaaaa tataacttac     300
taaagatgga gttcttgtga ctgactcctg atatcaagat actgggagcc aaattaaaaa     360
tcagaaggct gcttggagag caagtccatg aaatgctctt tttcccacag tagaacctat     420
ttccctcgtg tctcaaatac ttgcacagag gctcactccc ttggataatg cagagcgagc     480
acgatacctg gcacatacta atttgaataa aatgctgtca aattcccatt cacccattca     540
agcagcaaac tctatctcac ctgaatgtac atgccaggca ctgtgctaga cttggctcaa     600
aaagatttca gtttcctgga ggaaccagga gggcaaggtt tcaactcagt gctataagaa     660
gtgttacagg ctggacacgg tggctcacgc ctgtaatccc aacatttggg aggccgaggc     720
gggcagatca caaggtcagg agatcgagac catcctggct aacatggtga aaccctgtct     780
ctactaaaaa tacaaaaaat tagccgggcg ttggcggcag gtgcctgtag tcccagctgc     840
tggggaggct gaggcaggag aatggtgtga acccgggagg cggaacttgc aggggccga     900 gatcgtgcca ctgcactcca gcctgggcga cagagtgaga ctctgtctca aaaaaaaaaa     960
aaaagtgtta tgatgcagac ctgtcaaaga ggcaaaggag ggtgttccta cactccaggc    1020
actgttcata acctggactc tcattcattc tacaaatgga gggctcccct gggcagatcc    1080
ctggagcagg cactttgctg gtgtctcggt taaagagaaa ctgataactc ttggtattac    1140
caagagatag agtctcagat ggatattctt acagaaacaa tattcccact tttcagagtt    1200
caccaaaaaa tcattttagg cagagctcat ctggcattga tctggttcat ccatgagatt    1260
ggctagggta acagcacctg tcttgcagg gttgtgtgag cttatctcca gggttgcccc     1320
```

```
aactccgtca ggagcctgaa ccctgcatac cgtatgttct ctgccccagc caagaaaggt    1380
caattttctc ctcagaggct cctgcaattg acagagagct cccgaggcag agaacagcac    1440
ccaaggtaga gacccacacc ctcaatacag acagggaggg ctattggccc ttcattgtac    1500
ccatttatcc atctgtaagt gggaagattc ctaaacttaa gtacaaagaa gtgaatgaag    1560
aaaagtatgt gcatgtataa atctgtgtgt cttccacttt gtcccacata tactaaattt    1620
aaacattctt ctaacgtggg aaaatccagt attttaatgt ggacatcaac tgcacaacga    1680
ttgtcaggaa acaatgcat atttgcatgg tgatacattt gcaaatgtg tcatagtttg    1740 ctactccttg cccttccatg aaccagaaa ttatctcagt ttattagtcc cctcccctaa    1800
gaagcttcca ccaatactct tttcccctt cctttaactt gattgtgaaa tcaggtattc    1860
aacagagaaa tttctcagcc tcctacttct gcttttgaaa gctataaaaa cagcgaggga    1920
gaaactggca gataccaaac ctcttcgagg cacaaggcac aacaggctgc tctgggattc    1980
tcttcagcca atcttcattg ctcaagtatg actttaatct tccttacaac taggtgctaa    2040
gggagtctct ctgtctctct gcctctttgt gtgtatgcat attctctctc tctctctctt    2100
tctttctctg tctctcctct ccttcctctc tgcctcctct ctcagttttt tgcaaaaatg    2160
ccaggtgtaa tataatgctt atgactcggg aaatattctg ggaatggata ctgcttatct    2220
aacagctgac accctaaagg ttagtgtcaa agcctctgct ccagtctctcc tagccaatac    2280 attgctagtt ggggtttggt ttagcaaatg cttttctcta gacccaaagg acttctcttt    2340
cacacattca ttcatttact cagagatcat ttctttgcat gactgccatg cactggatgc    2400
tgagagaaat cacacatgaa cgtagccgtc atggggaagt cactcatttt ctccttttta    2460
cacaggtgtc tgaagcagcc atggcagaag tacctgagct cgccagtgaa atgatggctt    2520
attacaggtc agtggagacg ctgagaccag taacatgagc aggtctcctc tttcaagagt    2580
agagtgttat ctgtgcttgg agaccagatt ttttcccctaa attgcctctt tcagtggcaa    2640
acagggtgcc aagtaaatct gatttaaaga ctactttccc attacaagtc cctccagcct    2700
tgggacctgg aggctatcca gatgtgttgt tgcaagggct tcctgcagag gcaaatgggg    2760
agaaaagatt ccaagcccac aatacaagga atccctttgc aaagtgtggc ttggagggag    2820
agggagagct cagattttag ctgactctgc tgggctagag gttaggcctc aagatccaac    2880
agggagcacc agggtgccca cctgccaggc ctagaatctg ccttctggac tgttctgcgc    2940
atatcactgt gaaacttgcc aggtgtttca ggcagctttg agaggcaggc tgtttgcagt    3000
ttcttatgaa cagtcaagtc ttgtacacag ggaaggaaaa ataaacctgt ttagaagaca    3060
taattgagac atgtccctgt ttttattaca gtggcaatga ggatgacttg ttctttgaag    3120
ctgatggccc taaacagatg aaggtaagac tatgggttta actcccaacc caaggaaggg    3180
ctctaacaca gggaaagctc aaagaaggga gttctgggcc actttgatgc catggtattt    3240
tgttttagaa agactttaac ctcttccagt gagacacagg ctgcaccact tgctgacctg    3300
gccacttggt catcatatca ccacagtcac tcactaacgt tggtggtggt ggccacactt    3360
ggtggtgaca ggggaggagt agtgataatg ttcccatttc atagtaggaa gacaaccaag    3420
tcttcaacat aaatttgatt atccttttaa gagatggatt cagcctatgc caatcacttg    3480
agttaaactc tgaaaccaag agatgatctt gagaactaac atatgtctac cccttttgag    3540
tagaatagtt ttttgctacc tggggtgaag cttataacaa caagacatag atgatataaa    3600 caaaagatg aattgagact tgaaagaaaa ccattcactt gctgtttgac cttgacaagt    3660
catttacccc gctttggacc tcatctgaaa aataaagggc tgagctggat gatctctgag    3720
```

```
attccagcat cctgcaacct ccagttctga aatattttca gttgtagcta agggcatttg   3780
ggcagcaaat ggtcattttt cagactcatc cttacaaaga gccatgttat attcctgctg   3840
tcccttctgt tttatatgat gctcagtagc cttcctaggt gcccagccat cagcctagct   3900
aggtcagttg tgcaggttgg aggcagccac ttttctctgg ctttatttta ttccagtttg   3960
tgatagcctc ccctagcctc ataatccagt cctcaatctt gttaaaaaca tatttcttta   4020
gaagttttaa gactggcata acttcttggc tgcagctgtg ggaggagccc attggcttgt   4080
ctgcctggcc tttgccccc attgcctctt ccagcagctt ggctctgctc caggcaggaa   4140
attctctcct gctcaacttt cttttgtgca cttacaggtc tctttaactg tctttcaagc   4200
ctttgaacca ttatcagcct taaggcaacc tcagtgaagc cttaatacgg agcttctctg   4260
aataagagga aagtggtaac atttcacaaa aagtactctc acaggatttg cagaatgcct   4320
atgagacagt gttatgaaaa aggaaaaaaa agaacagtgt agaaaaattg aatacttgct   4380
gagtgagcat aggtgaatgg aaaatgttat ggtcatctgc atgaaaaagc aaatcatagt   4440
gtgacagcat tagggataca aaaagatata gagaaggtat acatgtatgg tgtaggtggg   4500
gcatgtacaa aaagatgaca agtagaatcg ggatttattc taaagaatag cctgtaaggt   4560
gtccagaagc cacattctag tcttgagtct gcctctacct gctgtgtgcc cttgagtaca   4620
cccttaacct ccttgagctt cagagaggga taatcttttt attttatttt attttatttt   4680
gttttgtttt gttttgtttt gtttatgag acagagtctc actctgttgc ccaggctgga   4740
gtgcagtggt acaatcttgg cttactgcat cctccacctc ctgagttcaa gcgattctcc   4800
ttcctcagtc tcctgaatag ctaggattac aggtgcaccc caccacaccc agctaatttt   4860
tgtattttta gtagagaagg ggtttcgcca tgttggccag gctggttttg aagtcctgac   4920
ctaaatgatt catccacctc ggcttcccaa agtgctggga ttacaggcat gagccaccac   4980
gcctggccca gagagggatg atctttagaa gctcggggatt cttcaagcc cttcctcct   5040 ctctgagctt tctactctct gatgtcaaag catggttcct ggcaggacca cctcaccagg   5100
ctccctccct cgctctctcc gcagtgctcc ttccaggacc tggacctctg ccctctggat   5160
ggcggcatcc agctacgaat ctccgaccac cactacagca agggcttcag gcaggccgcg   5220
tcagttgttg tggccatgga caagctgagg aagatgctgg ttccctgccc acagaccttc   5280
caggagaatg acctgagcac cttctttccc ttcatctttg aagaaggtag ttagccaaga   5340
gcaggcagta gatctccact tgtgtcctct tggaagtcat caagcccag ccaactcaat   5400 tcccccagag ccaaagccct ttaaaggtag aaggcccagc ggggagacaa aacaaagaag   5460
gctggaaacc aaagcaatca tctctttagt ggaaactatt cttaaagaag atcttgatgg   5520
ctactgacat ttgcaactcc ctcactcttt ctcaggggcc tttcacttac attgtcacca   5580
gaggttcgta acctccctgt gggctagtgt tatgaccatc accattttac ctaagtagct   5640
ctgttgctcg gccacagtga gcagtaatag acctgaagct ggaacccatg tctaatagtg   5700
tcaggtccag tgttcttagc cacccactc ccagcttcat ccctactggt gttgtcatca   5760
gactttgacc gtatatgctc aggtgtcctc caagaaatca aattttgcca cctcgcctca   5820
cgaggcctgc ccttctgatt ttatacctaa acaacatgtg ctccacattt cagaacctat   5880
cttcttcgac acatgggata acgaggctta tgtgcacgat gcacctgtac gatcactgaa   5940
ctgcacgctc cgggactcac agcaaaaaag cttggtgatg tctggtccat atgaactgaa   6000
agctctccac ctccagggac aggatatgga gcaacaaggt aaatggaaac atcctggttt   6060
ccctgcctgg cctcctggca gcttgctaat tctccatgtt ttaaacaaag tagaaagtta   6120
```

```
atttaaggca aatgatcaac acaagtgaaa aaaaatatta aaaaggaata tacaaacttt    6180
ggtcctagaa atggcacatt tgattgcact ggccagtgca tttgttaaca ggagtgtgac    6240
cctgagaaat tagacggctc aagcactccc aggaccatgt ccacccaagt ctcttgggca    6300
tagtgcagtg tcaattcttc cacaatatgg ggtcatttga tggacatggc ctaactgcct    6360
gtgggttctc tcttcctgtt gttgaggctg aaacaagagt gctggagcga taatgtgtcc    6420
atccccctcc ccagtcttcc cccttgccc caacatccgt cccacccaat gccaggtggt     6480
tccttgtagg gaaattttac cgcccagcag gaacttatat ctctccgctg taacgggcaa    6540
aagtttcaag tgcggtgaac ccatcattag ctgtggtgat ctgcctggca tcgtgccaca    6600
gtagccaaag cctctgcaca ggagtgtggg caactaaggc tgctgacttt gaaggacagc    6660
ctcactcagg gggaagctat ttgctctcag ccaggccaag aaaatcctgt ttctttggaa    6720
tcgggtagta agagtgatcc cagggcctcc aattgacact gctgtgactg aggaagatca    6780
aaatgagtgt ctctctttgg agccactttc ccagctcagc ctctcctctc ccagtttctt    6840
cccatgggct actctctgtt cctgaaacag ttctggtgcc tgatttctgg cagaagtaca    6900
gcttcacctc tttcctttcc ttccacattg atcaagttgt tccgctcctg tggatgggca    6960
cattgccagc cagtgacaca atggcttcct tccttccttc cttcagcatt taaaatgtag    7020
accctctttc attctccgtt cctactgcta tgaggctctg agaaaccctc aggcctttga    7080
ggggaaaccc taaatcaaca aaatgaccct gctattgtct gtgagaagtc aagttatcct    7140
gtgtcttagg ccaaggaacc tcactgtggg ttcccacaga ggctaccaat tacatgtatc    7200
ctactctcgg ggctaggggt tggggtgacc ctgcatgctg tgtccctaac cacaagaccc    7260 ccttcttct tcagtggtgt tctccatgtc ctttgtacaa ggagaagaaa gtaatgacaa     7320
aatacctgtg gccttgggcc tcaaggaaaa gaatctgtac ctgtcctgcg tgttgaaaga    7380
tgataagccc actctacagc tggaggtaag tgaatgctat ggaatgaagc ccttctcagc    7440
ctcctgctac cacttattcc cagacaattc accttctccc cgcccccatc cctaggaaaa    7500
gctgggaaca ggtctatttg acaagttttg cattaatgta aataaattta acataatttt    7560
taactgcgtg caaccttcaa tcctgctgca gaaaattaaa tcattttgcc gatgttatta    7620
tgtcctacca tagttacaac cccaacagat tatatattgt tagggctgct ctcatttgat    7680
agacaccttg ggaaatagat gacttaaagg gtcccattat cacgtccact ccactcccaa    7740
aatcaccacc actatcacct ccagctttct cagcaaaagc ttcatttcca agttgatgtc    7800
attctaggac cataaggaaa aatacaataa aaagcccctg gaaactaggt acttcaagaa    7860
gctctagctt aattttcacc ccccaaaaa aaaaaattc tcacctacat tatgctcctc       7920
agcatttggc actaagtttt agaaaagaag aagggctctt ttaataatca cacagaaagt    7980
tgggggccca gttacaactc aggagtctgg ctcctgatca tgtgacctgc tcgtcagttt    8040
cctttctggc caacccaaag aacatctttc ccataggcat ctttgtccct tgccccacaa    8100
aaattcttct ttctctttcg ctgcagagtg tagatcccaa aaattaccca agaagaaga    8160 tggaaaagcg atttgtcttc aacaagatag aaatcaataa caagctggaa tttgagtctg    8220
cccagttccc caactggtac atcagcacct ctcaagcaga aacatgccc gtcttcctgg     8280 gagggaccaa aggcggccag gatataactg acttcaccat gcaatttgtg tcttcctaaa    8340
gagagctgta cccagagagt cctgtgctga atgtggactc aatccctagg gctggcagaa    8400
agggaacaga aaggtttttg agtacggcta tagcctggac tttcctgttg tctacaccaa    8460
tgcccaactg cctgccttag ggtagtgcta agaggatctc ctgtccatca gccaggacag    8520
```

-continued

```
tcagctctct cctttcaggg ccaatcccca gcccttttgt tgagccaggc ctctctcacc    8580
tctcctactc acttaaagcc cgcctgacag aaaccacggc cacatttggt tctaagaaac    8640
cctctgtcat tcgctcccac attctgatga gcaaccgctt ccctatttat ttatttattt    8700
gtttgtttgt tttgattcat tggtctaatt tattcaaagg gggcaagaag tagcagtgtc    8760
tgtaaaagag cctagttttt aatagctatg gaatcaattc aatttggact ggtgtgctct    8820
ctttaaatca agtcctttaa ttaagactga aaatatataa gctcagatta tttaaatggg    8880
aatatttata aatgagcaaa tatcatactg ttcaatggtt ctgaaataaa cttcactgaa    8940
gaaaaaaaaa aaagggtctc tcctgatcat tgactgtctg gattgacact gacagtaagc    9000
aaacaggctg tgagagttct tgggactaag cccactcctc attgctgagt gctgcaagta    9060
cctagaaata tccttggcca ccgaagacta tcctcctcac ccatcccctt tatttcgttg    9120
ttcaacagaa ggatattcag tgcacatctg gaacaggatc agctgaagca ctgcagggag    9180
tcaggactgg tagtaacagc taccatgatt tatctatcaa tgcaccaaac atctgttgag    9240
caagcgctat gtactaggag ctgggagtac agagatgaga acagtcacaa gtccctcctc    9300
agataggaga ggcagctagt tataagcaga acaaggtaac atgacaagta gagtaagata    9360
gaagaacgaa gaggagtagc caggaaggag ggaggagaac gacataagaa tcaagcctaa    9420
agggataaac agaagatttc cacacatggg ctgggccaat tgggtgtcgg ttacgcctgt    9480
aatcccagca ctttgggtgg caggggcaga aagatcgctt gagcccagga gttcaagacc    9540
agcctgggca acatagtgag actcccatct ctacaaaaaa taaataaata aataaaacaa    9600
tcagccaggc atgctggcat gcacctgtag tcctagctac ttgggaagct gacactggag    9660
gattgcttga gcccagaagt tcaagactgc agtgagctta tccgttgacc tgcaggtcga    9720
c                                                                   9721
```

US 7,732,134 B2

METHODS TO PREDICT CHOLESTEROL ELEVATION DURING IMMUNOSUPPRESSANT THERAPY

This application claims benefit of U.S. Provisional Application No. 60/415,123, which was filed on Sep. 30, 2002.

BACKGROUND OF THE INVENTION

1. Field of the Invention

The present invention belongs to the fields of pharmacology and medicine and provides methods to determine which patients will develop elevated serum cholesterol levels during treatment with an immunosuppressant drug. In particular, this invention relates to the use of genomic analysis to identify patients at risk for developing increased cholesterol levels during immunosuppressant drug therapy and to methods to determine optimal treatment strategies for these patients.

2. Description of the Related Art

Immunosuppressant drugs have many important applications in modern medicine. These drugs are used to suppress the rejection of transplanted organs, including hearts, lungs and kidneys to prolong the useful life of the transplanted organ. In addition, immunosuppressant drugs are used to treat a wide variety of other diseases such as autoimmune diseases, myocarditis and rheumatoid arthritis. However, the immunosuppressant drugs have numerous, and sometimes severe, side effects which include causing cancer and lymphomas and producing a variety of toxic effects on internal organs, such as the kidney.

Because of the toxic effect of the immunosuppressant drugs, there has been a great deal of effort to develop less toxic alternatives and to find drugs whose mechanism of action differs from that of the other immunosuppressant drugs so that synergistic combinations can be used with fewer overall side effects.

Recently an anti-fungal, anti-tumor and immunosuppressive antibiotic called rapamycin (also known as sirolimus and RAPAMUNE™) has been found to be effective at inhibiting allograft rejection. Rapamycin has a mechanism of action that is unique and markedly different from that of other immunosuppressant drugs. Rapamycin and its derivatives, such as everolimus (CERTICAN™)(RAD) act by inhibiting the biochemical pathways involved in the G1-S phase progression of activated T cells in a $Ca^{2+}$ independent manner. See Schuler et al., *Transplantation*, Vol. 64, pp. 36-42 (1997). In this way, rapamycin derivatives such as everolimus block cytokine signal transduction rather than blocking the production of cytokines as in the case of other immunosuppressant drugs, such as cyclosporine.

Rapamycin and its derivatives and mycophenolic acid are effective immunosuppressant drugs, however, in some patients the administration of these drugs has been found to cause elevations in serum cholesterol and triglycerides, i.e., hypercholesterolemia and hyperlipidemia. Both of these conditions are risk factors for coronary artery disease (CAD) and atherosclerosis in general, especially in diabetic patients.

Hypercholesterolemia itself, is a common condition and can be treated with several major classes of drugs. These include the HMG-CoA reductase inhibitors or the so-called statins, the bile acid-binding resins and nicotinic acid.

Increased serum cholesterol levels during treatment with an immunosuppressant drug, such as rapamycin or its derivatives including, but not limited to, everolimus (CERTICAN™)(RAD) or with mycophenolic acid, is a serious adverse side effect. This is especially true for organ transplant patients since these patients require long-term (generally life long) treatment. The increase in serum cholesterol levels varies widely from patient to patient and prior to the present invention it was not possible to predict which patients would develop these increases. Thus, there is a need for methods to predict which patients will experience elevations in serum cholesterol when immunosuppressant drugs, such as rapamycin and its derivatives or mycophenolic acid are administered to patients, especially for long-term use.

SUMMARY OF THE INVENTION

The present invention overcomes this problem by providing a method to determine the degree of serum cholesterol elevation which will occur in a patient during treatment with an immunosuppressant medication comprising: determining for the two copies of the IL-1β gene present in the patient the identity of the nucleotide pair at the polymorphic site -511 CT (position 1423 of sequence X04500, which is incorporated by reference and is SEQ ID NO:11 of the sequence listing) of the IL-1β gene; and assigning the patient to a high cholesterol elevation group if both pairs are AT, assigning the patient to an intermediate cholesterol elevation group if one pair is AT and one pair is GC and assigning the patient to a low cholesterol elevation group if both pairs are GC.

In a further embodiment this invention provides another method to treat a patient with an immunosuppressive medication comprising: determining for the two copies of the IL-1β gene present in the patient the identity of the nucleotide pair at the polymorphic site -511 CT (position 1423 of sequence X04500, which is incorporated by reference and is SEQ ID NO:11 of the sequence listing) of the IL-1β gene; and treating the patient with the immunosuppression medication if both pairs are GC and using alternative treatment if one pair is AT and one pair is GC or if both pairs are AT. The immunosuppressive medication may be selected from the list in Table 2 and may be everolimus. In addition this invention provides that the alternative treatment comprises the addition of a cholesterol-lowering medication chosen from those listed in Table 1.

In a further embodiment this invention provides a method to determine the degree of serum cholesterol elevation which will occur in a patient during treatment with an immunosuppressant medication comprising: determining for the two copies of the IL-1β gene present in the patient the identity of the nucleotide pair at the polymorphic site -31 TC (position 1903 of sequence X04500, which is incorporated by reference and is SEQ ID NO:11 of the sequence listing) of the IL-1β gene; and assigning the patient to a high cholesterol elevation group if both pairs are CG, assigning the patient to an intermediate cholesterol elevation group if one pair is AT and one pair is GC and assigning the patient to a low cholesterol elevation group if both pairs are AT.

In a still further embodiment this invention provides a method to treat a patient with an immunosuppressive medication comprising: determining for the two copies of the IL-1β gene present in the patient the identity of the nucleotide pair at the polymorphic site -31 TC (position 1903 of sequence X04500, which is incorporated by reference and is SEQ ID NO:11 of the sequence listing) of the IL-1β gene; and treating the patient with the immunosuppression medication if both pairs are AT and using alternative treatment if one pair is AT and one pair is GC or if both pairs are CG, The immunosuppressive medication may be selected from the list in Table 2 and may be everolimus. In addition the alternative treatment may comprise the addition of a cholesterol-lowering medication chosen from those listed in Table 1.

In a still further embodiment this invention provides a kit for determining the nucleotide pair at the polymorphic site -511 in the IL-1β gene in a patient, comprising: a container containing at least one reagent specific for detecting the nature of the nucleotide pair at the polymorphic site -511 of the IL-1β gene; and instructions for recommended treatment options based on the nature of the said nucleotide pair.

In a still further embodiment this invention provides a kit for determining the nucleotide pair at the polymorphic site -31 in the IL-1β gene in a patient, comprising: a container containing at least one reagent specific for detecting the nature of the nucleotide pair at the polymorphic site -31 of the IL-1β gene; and instructions for recommended treatment options based on the nature of the said nucleotide pair.

In a further embodiment this invention provides a method to determine the degree of serum cholesterol elevation which will occur in a patient during treatment with an immunosuppressant medication comprising determining, for the two copies, containing the IL-1β gene, present in the patient, the haplotype with regard to the IL-1β gene. The term "haplotype with regard to the IL-1 gene" shall refer to the haplotype consisting of the combination of the polymorphisms at the -511 and the -31 position of the IL-1β gene. The patient would be assigned to a high cholesterol elevation group if both chromosomes contain the "high cholesterol" haplotype i.e., T for C at site -511 and C for T at site -31 of the IL-1β gene, and the patient would be assigned to an intermediate cholesterol elevation group if one chromosome contains the "high cholesterol" haplotype and one contains the "low cholesterol" haplotype and the patient would be assigned to a low cholesterol elevation group if both chromosomes contain the "low cholesterol" haplotype, i.e. C at site -511 and T at site -31.

In a still further embodiment this invention provides a method to treat a patient with an immunosuppressive medication comprising determining, for the two chromosomes containing the IL-1β gene, present in the patient, the haplotype with regard to the IL-1β gene, and treating the patient with the immunosuppression medication if both chromosomes contain the "low cholesterol" haplotype or if one chromosome contains the "low cholesterol" haplotype and one contains the "high cholesterol" haplotype and using alternative treatment if both chromosomes contain the "high cholesterol" haplotype. The immunosuppressive medication may be selected from the list in Table 2 and may be everolimus. The alternative treatment may comprise the addition of a cholesterol-lowering medication chosen from those listed in Table 1.

In a further embodiment this invention provides methods of determining the identity of the nucleotide pair at the site -511 and -31 of the IL-1β gene in a patient or the haplotype of the IL-1β gene in a patient by finding SNPs anywhere in the chromosome which are in linkage disequilibrium with the -511 polymorphism or the -31 polymorphism in the IL-1β gene and using the relationship of the said SNP or SNPs to determine the nature of the nucleotide pair or haplotype of interest and using this information to estimate cholesterol elevation during IM therapy and to make treatment decisions.

A further embodiment of this invention is a kit for determining the nature of the haplotype of the IL-1β gene which includes; a container containing at least one reagent specific for detecting the nature of the nucleotide pair at the polymorphic site -511 of the IL-1β gene; and a container containing at least one reagent specific for detecting the nature of the nucleotide pair at the polymorphic site -31 of the IL-1β gene; and instructions for determining the haplotype from the results of the above and instructions for recommended treatment options based on the nature of the indicated haplotype.

DETAILED DESCRIPTION OF THE INVENTION

Figure 1:
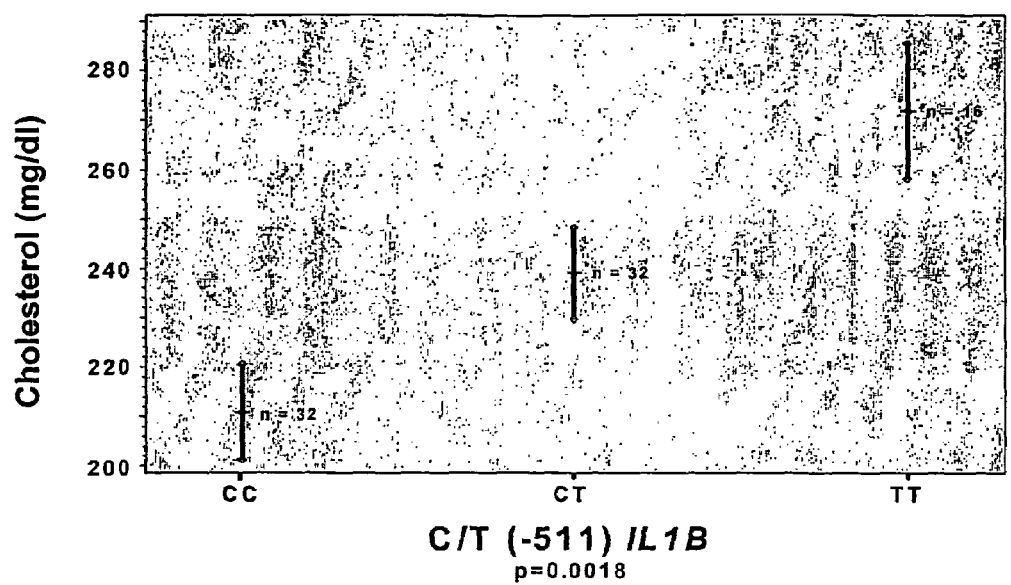
FIG. 1: LS mean total cholesterol levels compared to the (-511) IL-1β CC, CT or TT genotypes in all treatment groups combined within the RAD B251 clinical trial.

The present invention provides methods to determine the degree of serum cholesterol elevation that will occur in a patient during treatment with an immunosuppressant medication (IM), such as rapamycin or its derivatives.

In one embodiment, a patient who is a potential candidate for treatment with an IM would have blood drawn for a determination of the presence of a polymorphism, i. e., cytosine (C) thymine (T) at nucleotide position -51 1 (in the promoter region with no amino acid change); this is a C T change at nucleotide position 1423 of sequence X04500, which is incorporated by reference and is SEQ ID NO:11 of the sequence listing, in the two copies of the interleukin-1-beta (IL-1β ) gene present in the patient. If the nucleotide pair at position -511 is AT in both copies of the gene, then the patient will experience a high elevation in serum cholesterol levels during treatment with an IM.

If the nucleotide pair at position -511 is AT in one copy and CG in the other copy, then the patient will have an intermediate elevation in their cholesterol levels during treatment with an immunosuppressant medication.

If the nucleotide pair is GC at both copies at position -511, then the patient will have a low elevation in serum cholesterol levels during treatment with an IM.

In another embodiment, a determination of which medications to use to treat a patient in need of treatment with an IM would be based on the results of the determination of the nature of the nucleotide pairs at position -511 in the IL-1β gene present in the patient.

If both nucleotide pairs are GC then the patient would be treated with an IM. This immunosuppressant medication could be any of those shown in Table 2, including rapamycin or one of its derivatives, including, but not limited to, everolimus (Certican™)(RAD).

If both nucleotide pairs are AT, or if one pair is AT and one pair is GC, then the patient would be treated with an alternative medication that did not raise cholesterol levels or alternatively the patient would be treated with a cholesterol-lowering drug in addition to the IM and the patients' cholesterol levels would be monitored during treatment. This cholesterol-lowering drug, which would be used in combination with IM, could be one or more of the medications chosen from the list in Table 1 below.

In a further embodiment, a patient who is a potential candidate for treatment with an IM would have blood drawn for a determination of the presence of a polymorphism TC at nucleotide position -31 (in the promoter region with no amino acid change); this is a TC change at nucleotide position 1903 of sequence X04500, which is incorporated by reference and is SEQ ID NO:11 of the sequence listing, in the two copies of the IL-1β gene present in the patient. If the nucleotide pair at position -31 is a CG in both copies of the gene, then the patient will experience a high elevation in serum cholesterol levels during treatment with an IM. If the nucleotide pair at position -31 is AT in one copy and CG in the other copy, then the patient will have an intermediate elevation in their cholesterol levels during treatment with an IM. If the nucleotide pair is AT at both copies at position -31, then the patient will have a low elevation in serum cholesterol levels during treatment with an IM.

In another embodiment, a determination of which medications to use to treat a patient in need of treatment with an IM would be based on the results of the determination of the nature of the nucleotide pairs at position -31 in the IL-1 gene present in the patient. If both nucleotide pairs are AT then the patient would be treated with an IM.

This IM could any of those shown in Table 2 including, but not limited to, rapamycin or one of its derivatives including, but not limited to, everolimus (CERTICAN™) (RAD).

If both nucleotide pairs are GC or if the nucleotide pair is AT in one copy and CG in the other copy, then the patient would be treated with an alternative medication that did not raise cholesterol levels or alternatively the patient would be treated with a cholesterol-lowering drug in addition to the IM and the patients' cholesterol levels would be monitored during treatment. This cholesterol-lowering drug, which would be used in combination with IM, could be one or more of the medications chosen from the list in Table 1 below.

Suitable rapamycins for use in the methods of this invention are, e.g., as described in U.S. Pat. Nos. 3,929,992 and 5,258,389 and in WO 94/09010 and WO 01/60345, all of which are hereby incorporated by reference in their entirety and for all purposes.

TABLE 1

Antilipemic Agents (Cholesterol-Lowering Drugs)

Bile Acid Sequestrants

Colestipol (COLESTID ™ Pharmacia & Upjohn)
Fibric Acid Derivatives

Clofibrate (ATROMID-S ™ Wyeth-Ayerst)
Gemfibrozil (LOPID ™ Park-Davis)
Fenofibrate (TRICOR ™ Abbott)
HMG-CoA Reductase Inhibitors Fluvastatin (LESCOL ™ Novartis)
Atorvastatin (LIPITOR ™ Parke-Davis)
Lovastatin (MEVACOR ™ Merck)
Pravastatin (PRAVACOL ™ Bristol-Myers Squibb)
Simvastatin (ZOCOR ™ Merck)
Nicotinic Acid Niacin (NIASPAN ™ Kos)

TABLE 2

Immunosuppressant Drugs

Rapamycin (sirolimus, RAPAMUNE ™)
Everolimus (CERTICAN ™) (RAD)
Mycophenolic acid and Mycophenolate Mofetil (CELLCEPT ™) (MMF)
Azathioprine (IMURAN ™)
Cyclosporine (NEORAL ™)
Tacrolimus (PROGRAF ™)

The following example is provided for the purpose of further illustration only and is not intended to be a limitation on the disclosed invention.

EXAMPLE 1

The RAD B251 Study

Overall Study Design

The RAD B251 study was a randomized, multicenter, double-blind, parallel group study of the efficacy and safety of everolimus (Certican™) (RAD) versus mycophenolate mofetil (MMF) used in combination with cyclosporine (CsA) (NEORAL®) and prednisone. The study consisted of three periods: a Screening period, a Baseline period and a Double-Blind Treatment period. Following the Baseline assessments, patients who meet the inclusion/exclusion criteria were randomized into one of the three treatment groups (1:1:1) once it has been ascertained that the allograft is functional and that oral medication can be tolerated (within 48 hours post-transplantation). Determination of allograft function was by the investigator's judgement and was based upon adequate urine output and evidence of falling creatinine levels. The day of randomization and administration of the first dose of study medication was recorded as Day 1 of the study. The three treatment groups are described below:

Dose Level 1: 0.75 mg RAD bid+NEORAL®+prednisone
Dose Level 2: 1.5 mg RAD bid+NEORAL®+prednisone
Comparator 1 g MMF bid+NEORAL®+prednisone Concomitant Therapy Initiation and Maintenance of NEORAL®

Oral CsA (NEORAL®) administration was begun at 6-12 mg/kg/day p.o. and was adjusted to maintain a 12-hour trough level reflecting a standard target assay range. Intravenous (i.v.) administration of CsA was avoided unless mandated by the clinical situation. Whole blood levels were brought into the therapeutic ranges listed below as rapidly as possible. Once this was achieved, doses of CsA were only adjusted for maintaining trough blood levels within the target ranges.

Weeks 1-4: 200-350 ng/mL
Months 2-36: 100-300 ng/mL

On the days when blood for CsA or RAD measurements was to be drawn, the patient received the prior dose of NEORAL® and study medication 12±1 hour prior to the blood draw. The patients were instructed to adjust their medication schedule on the day previous to the blood draw to achieve proper timing and the exact time of administration of the evening dose was recorded. Study medication and NEORAL® due on the day of the blood draw were not to be taken by the patient, but were brought to the clinic and taken after the blood draw was completed.

Prednisone

Immediately prior to transplant, patients could receive up to 1 g methylprednisolone i.v. and then up to 500 mg methylprednisolone i.v. 12 hours later. As soon as possible post-transplantation, oral prednisone was initiated at 0.35-2.0 mg/kg/day and tapered in order to achieve a dose of 20 mg/day, or 0.25 mg/kg/day, by Day 30 and of no less than 5 mg/day for the first six months.

Cytomegalovirus (CMV) Prophylaxis

CMV prophylaxis was mandatory for all cases in which the donor tests positive and the recipient tests negative for CMV. Treatment with ganciclovir, CMV hyperimmune globulin or acyclovir was permitted and was administered according to local practice. All cases other than CMV positive donors to CMV negative recipients were treated according to local practice. CMV prophylaxis was also recommended following any antibody treatment of acute rejection episodes.

PCP Prophylaxis

All patients were also started on trimethoprim-sulfamethoxazole, one single strength tablet per day, starting when oral medication could be tolerated and continuing for the first six months after transplantation. Dosage was decreased at the investigator's discretion to one single strength tablet 3 times a week for the second six months. Treatment after one year was according to local practice. Aerosolized pentamidine or dapsone was administered to patients unable to tolerate trimethoprim-sulfamethoxazole.

Other Concomitant Therapy

No medication other than the study drugs, study prophylaxis and the usual medications of the patients were given during the full treatment period of the study, i.e., from the initial day of screening until all of the final study evaluations have been completed. Exceptions to this rule applied only to medications that were needed to treat adverse events (AEs). The administration of any additional medication (including over-the-counter medications and vitamins) were clearly documented on the Prior and Concomitant Medications Case Report Form (CRF). If required for an AE, concomitant medications were clearly documented and cross-referenced on the AEs CRF.

All immunosuppressive drugs other than those specified by protocol were disallowed. Permissible anti-rejection therapy includes methylprednisolone and anti-lymphocyte antibody therapy according to the guidelines in "Treatment of Acute Rejection Episodes". Patients requiring tacrolimus or MMF for rescue therapy were discontinued from study drug. Terfenadine, astemizole and cisapride were prohibited while the patient is on study medication. The use of phenobarbital, phenytoin, carbamazepine, or ketoconazole was strongly discouraged.

A treatment period of three years followed transplantation. During the Double-Blind Treatment period, the patients were seen at Days 7, 14 and 28 and at Months 2, 3, 6, 9, 12, 18, 24, 30 and 36. Renal biopsies were required at Baseline (may be intra-operative) and at the time of any suspected rejection. Blinded study drug administration ceased at 3 years.

Male and female patients, 16-65 years of age who are scheduled to undergo primary cadaveric, living unrelated or non-HLA identical related donor kidney transplantation, were allowed to enter the study. Patients who discontinued the study prematurely were not replaced. Each patient had to meet all of the inclusion/exclusion criteria to be eligible for entry into the study.

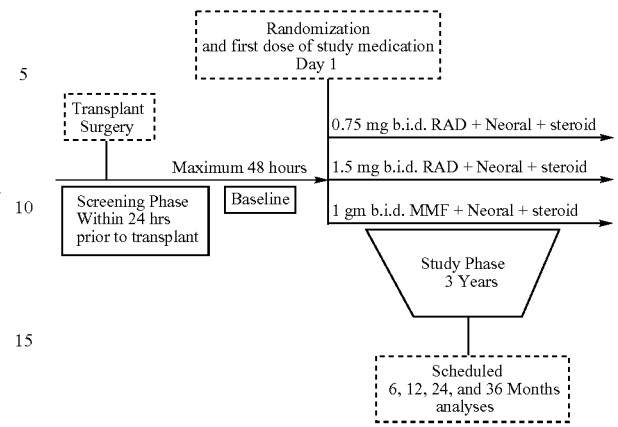

The RAD B251 study was designed to assess the safety and efficacy of two oral doses of RAD compared to MMF in de novo renal transplant recipients as measured by the incidence of biopsy proven acute allograft rejection episodes, graft loss or death. MMF was chosen as the comparator agent because of its widespread use in renal transplantation.

Pharmacogenetics Analysis

In an effort to identify genetic factors that are associated with increased cholesterol and lipid levels observed in patients treated with everolimus (RAD), 47 single nucleotide polymorphisms (SNPs) from 24 genes within genomic polydeoxribonucleotide (DNA) of patients participating in the RAD B251 clinical trials were examined. Of the 47 SNPs that were examined, 21 were experimentally determined to be not polymorphic. Of the 26 that were polymorphic, two SNPs in the IL-1β gene promoter at positions (-511) and (-31) showed statistical significance in relation to changes in cholesterol levels in patients participating in the RAD B251 clinical trial.

Patients who were homozygous for the IL-1β (-511) C→T base transition (T-T) or the IL-1β (-31) T→C base transition (C-C) had the highest least mean levels of total cholesterol at their last visit regardless of treatment received during the study (p=0.0018 and p=0.0013 respectively). (The values on the figures, etc. refer to the absolute serum cholesterol levels at the last visit, however during the statistical analysis this value was defined as the dependent variable and the cholesterol level at baseline as the independent variable thus automatically taking into consideration the baseline level).

The increase in total cholesterol levels was due to both increased levels of HDL and LDL: patients homozygous for the T allele at the (-511) position or the C allele at the (-31) position had the highest least square mean levels of HDL (p=0.0214 and p=0.0514 respectively) and LDL (p=0.0159 and p=0.0091 respectively) at their last visit. Importantly, however, the HDL to LDL ratios remained the same regardless of genotype.

Therefore, our findings suggest that individuals homozygous for the T allele at position (-511) and homozygous for the C allele at position (-31) of the IL-1β gene promoter may be predisposed to larger increases in total blood cholesterol levels upon treatment with either the RAD/NEORAL® or MMF/NEORAL® regimens.

Methods

Samples

A total of 82 unique samples from the RAD B251 clinical trial were genotyped upon their consent to participate in the pharmacogenetic evaluation. This represents about 15% of the total population that participated in the RAD B251 clinical trial. Blood samples from each patient were collected at the individual trial sites and then shipped to Covance (Geneva, Switzerland). The genomic DNA of each patient was extracted from the blood by Covance using the PURE-GENE™ DNA Isolation Kit (D-50K) (Gentra, Minneapolis, Minn.).

Genotyping

A total of 47 unique polymorphisms corresponding to 24 genes were analyzed for each clinical trial. Candidate genes involved in metabolism of the drug, hypercholesterolemia, hyperlipidemia, immunosuppression and inflammation were chosen for this study. SNP assays were designed using information from public databases, such as OMIM, the SNP Consortium, Locus Link and dbSNP, and the Third Wave Technologies, Inc. (TWT, Madison, Wis.) website (64.73.25.65:8080/coe/index.jsp). The resulting probe sets for the genotyping assay were generated by TWT. Genotyping was performed with 60 ng of genomic DNA using the INVADER® assay developed by TWT (9-10) according to the manufacturer's instructions. See Lyamichev et al., *Nat Biotechnol.*, Vol. 17, pp. 292-296 (1999); and Ryan, *Mol. Diagn.*, Vol. 4, pp. 135-144 (1999).

Polymerase Chain Reaction (PCR) for the (-511) IL-1β SNP was performed in a 20 μL reaction containing: 10-70 ng genomic DNA, 160 μM dNTPs, 10 mM Tris-HCl [pH 8.3], 50 mM KCl, 1.5 mM MgCl$_2$, 0.6 μM IL-1β(-511)-forward primer, 0.6 μM IL-1β(-511)-reverse primer and 0.03 U Taq DNA polymerase (Applied Biosystems, Foster City, Calif.). Thirty-six (36) rounds of amplification were performed using the following conditions: 94° C., 30 seconds; 55° C., 30 seconds; 72° C., 30 seconds. Nine samples were then fractionated (5 μL) on a 2% agarose gel and visualized by ethidium bromide staining to confirm amplification. A 1:7 dilution of the PCR product was run against TWT SNP#128069 using a 384-well biplex plate for amplified DNA.

Primer sequences are as follows:

(SEQ ID No.1)
IL-1β(-511)-forward 5'-GCAGAGCTCATCTGGCATTG-3';

(SEQ ID No.2)
IL-1β(-511)-reverse 5'-TATGTGGGACAAAG TGGAAG-3'.

PCR for the (-31) IL-1β SNP was performed in a 25 μL reaction containing: 1 ng genomic DNA, 40 μM dNTPs, 10 mM Tris-HCl [pH 8.3], 50 mM KCl, 1.5 mM MgCl$_2$, 0.75 μM IL-1β(-31)-forward primer, 0.75 μM IL-1β(-31)-reverse primer and 0.15 U Gold Taq DNA polymerase (Applied Biosystems, Foster City, Calif.). Thirty-eight (38) rounds of amplification were performed using the following conditions: 94° C., 30 seconds; 58° C., 30 seconds; 72° C., 30 seconds. All samples were then fractionated (5 μL) on a 2% agarose gel and visualized by ethidium bromide staining to confirm amplification.

Primer sequences are as follows:

(SEQ ID No.3)
IL-1β(-31)-forward 5'-GCACAACGATTGTCAGGAAAAC-3';

(SEQ ID No.4)
IL-1β(-31)-reverse (5'-ATGCATACA CACAAAGAGGCAG-3'.

A 1:10 dilution of the PCR product was run against TWT SNP# 274339 for RAD B251 using a 384-well biplex plate for amplified DNA. RFLP analysis was used to determine genotypes using the Alu-I restriction enzyme (New England Biolabs, Beverly, Mass.). RFLP digests were performed in a 20 μL reaction containing: 50 mM NaCl, 10 mM Tris-HCl, 10 mM MgCl$_2$, 1 mM DTT [pH 7.9], 8 ng amplified genomic DNA and 0.5 mM Alu-I enzyme. All samples were incubated for 17 hours at 37° C. and then fractionated (19 μL) on a 3% agarose gel and visualized by ethidium bromide staining to determine band size.

| Nucleotide sequence surrounding the (-511) IL-1β polymorphism | | | | |
|---|---|---|---|---|
| Gene | Position | Allele 1 | Allele 2 | Surrounding Sequence |
| IL-1β | -511 | C | T | CTGCAATTGACAGAGAGCT CC[C,T]GAGGCAGAGAAC AGCACCCAAGGTAGAGACC CA (SEQ ID No. 9) |

Allele 1 (SEQ ID No. 5);
CTGCAATTGACAGAGAGCTCC[C]GAGGCAGAGAACAGCACCCAAGGTAG
AGACCCA Allele 2 (SEQ ID No. 6);
CTGCAATTGACAGAGAGCTCC[T]GAGGCAGAGAACAGCACCCAAGGTAG
AGACCCA

| Nucleotide sequence surrounding the (-31) IL-1β polymorphism | | | | |
|---|---|---|---|---|
| Gene | Position | Allele 1 | Allele 2 | Surrounding Sequence |
| IL-1β | -31 | C | T | TCCTACTTCTGCTTTTGAA AGC[T,C]ATAAAAACAGC GAGGGAGAAACTGGCAGAT ACCAAACCTC (SEQ ID No. 10) |

Allele 1 (SEQ ID No. 7)
TCCTACTTCTGCTTTTGAAAGC[C]ATAAAAACAGCGAGGGAGAAACTGG
CAGATACCAAACCTC Allele 2 (SEQ ID No. 8)
TCCTACTTCTGCTTTTGAAAGC[T]ATAAAAACAGCGAGGGAGAAACTGG
CAGATACCAAACCTC Statistical Analysis An analysis of covariance model was used for the analysis of the effect of genotype and treatment on cholesterol levels using the 24-month lab_b.sd2 RADB 251 clinical data set. Terms in the model include the final cholesterol level, the initial cholesterol level as the covariant, and the genotype and treatment as the main effectors. The odds ratios, 95% confidence limits, and Chi-square analysis were calculated where applicable. All statistical analyses were performed using the SAS 8.02 software. To correct for multiple testing, the Bonferroni correction method was performed.

Results

In the RAD B251 study, 47 unique SNPs corresponding to 24 genes were genotyped for each patient consenting to pharmacogenetics analysis participating in the RAD B251 clinical trial. A comparison of the patients that consented to pharmacogenetics analysis to the overall patient distribution for each respective clinical trial is shown in Table 3.

TABLE 3

RAD B251: Distribution of Pharmacogenetic Samples Compared to the Overall Clinical Trial Samples

|  | Pharmacogenetic samples | Trial Samples |
|---|---|---|
| Age (years) | 43.34 | 43.49 |
| Race | | |
| Caucasian | (61) 74% | (388) 68% |
| Black | (9) 11% | (93) 16% |
| Oriental | (0) 0% | (11) 2% |
| Other | (12) 15% | (76) 13% |
| Gender | | |
| Male | (51) 62% | (357) 63% |
| Female | (31) 38% | (211) 37% |
| Treatment | | |
| RAD001(1.5 mg/d) | (24) 29.3% | (189) 33.3% |
| RAD001(3.0 mg/d) | (29) 35.3% | (189) 33.3% |
| MMF (2 g/d) | (29) 35% | (190) 33.4% |
| Weight (kg) | 80.7 | 77.1 |
| Baseline | | |
| CHO (mg/dL) | 168.7 | 162.8 |
| HDL (mg/dL) | 40.9 | 40.8 |
| LDL (mg/dL) | 96.6 | 96.8 |
| TGC (mg/dL) | 155.3 | 119.9 |
| End of treatment | | |
| CHO (mg/dL) | 234.5 | 232.2 |
| HDL (mg/dL) | 52.7 | 53.3 |
| LDL (mg/dL) | 123.2 | 126.6 |
| TGC (mg/dL) | 283.0 | 254.6 |

Only one statistically significant difference was found between the patient population used in the pharmacogenetic study compared to the overall patient population in the RAD B251 clinical trial: the differences in the mean TGC values among the pharmacogenetic patent population and the overall RAD B251 patient population were found to be statistically significant ($p<0.001$). This comparison therefore suggests that the patient population used in the pharmacogenetic study is representative of the overall patient population tested in each trial. Of the 47 SNPs that were tested in this study, 21 were experimentally determined to be not polymorphic. Therefore, 26 SNPs were used in the analysis described below.

Statistical analysis of the genotypes with the RAD B251 clinical data set identified a polymorphism within the IL-1β gene promoter at position (-511) that had a significant association with cholesterol levels. As shown in Table 4 and FIG. 1, the IL-1β (-511) (TT) genotype in patients from both treatment groups together correlated with the highest increase in levels of total cholesterol measured at their last visit ($p=0.0018$).

TABLE 4

LS Mean Total Cholesterol Levels (mg/dL) by (−511) IL-1β CC, CT or TT Genotypes and Treatment Groups Within the RAD B251 Clinical Trial

| | RAD (1.5 and 3.0 mg/day) | | | MMF (2 mg/day) | | | RAD and MMF treatment groups combined | | |
|---|---|---|---|---|---|---|---|---|---|
| Genotype | CC | CT | TT | CC | CT | TT | CC | CT | TT |
| No. of patients | 20 | 25 | 9 | 12 | 9 | 7 | 32 | 34 | 16 |
| LS means | 217.3 | 242.9 | 290.3 | 200.9 | 229.6 | 254.1 | 211.4 | 239.5 | 272.9 |
| P-value | 0.0125 | 0.0125 | 0.0125 | 0.0866 | 0.0866 | 0.0866 | 0.0018 | 0.0018 | 0.0018 |

Figure 2:
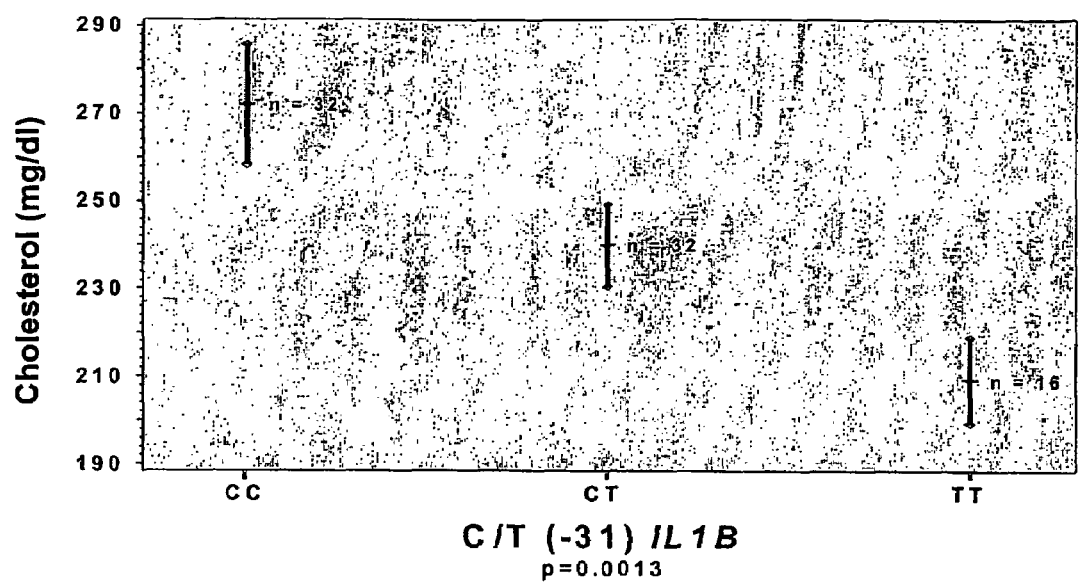
FIG. 2: LS mean total cholesterol levels compared to the (-31) IL-1β CC, CT or TT genotypes in all treatment groups combined within the RAD B251 clinical trial.

A similar association was observed for the IL-1 (-31) (C-C) genotype ($p=0.0013$) (Table 5 and FIG. 2).

TABLE 5

LS Mean Total Cholesterol Levels (mg/dL) by (−31) IL-1β CC, CT or TT Genotypes and Treatment Groups Within the RAD B251 Clinical Trial

| | RAD (1.5 and 3.0 mg/day) | | | MMF (2 mg/day) | | | RAD and MMF treatment groups combined | | |
|---|---|---|---|---|---|---|---|---|---|
| Genotype | CC | CT | TT | CC | CT | TT | CC | CT | TT |
| No. of patients | 9 | 26 | 19 | 7 | 9 | 12 | 16 | 35 | 31 |
| LS means | 291.1 | 240.4 | 216.6 | 254.1 | 239.6 | 200.9 | 272.9 | 239.5 | 211.4 |
| P-value | 0.009 | 0.009 | 0.009 | 0.0625 | 0.0625 | 0.0625 | 0.0013 | 0.0013 | 0.0013 |

Figure 3:
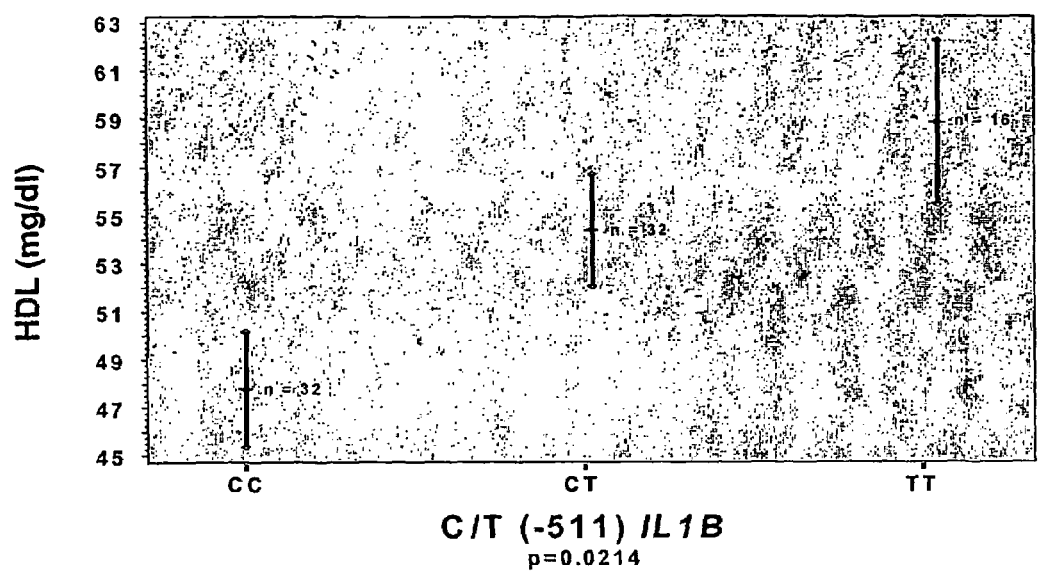
FIG. 3: LS mean HDL cholesterol levels compared to the (-511) IL-1β CC, CT or TT genotypes in all treatment groups combined within the RAD B251 clinical trial.

To analyze this correlation further, it was tested whether an association existed between the IL-1β (-511) genotype and levels of HDL and LDL. As shown in FIG. 3 and Table 6, the IL-1β (-511) (T-T) genotype in patients from both treatment groups together correlated with the highest levels of HDL measured at their last visit (p=0.0214).

TABLE 6

LS Mean HDL levels (mg/dL) by (−511) IL-1β CC, CT or TT Genotypes and Treatment Groups Within the RAD B251 Clinical Trial

|  | RAD (1.5 and 3.0 mg/day) | | | MMF (2 mg/day) | | | RAD and MMF treatment groups combined | | |
|---|---|---|---|---|---|---|---|---|---|
| Genotype | CC | CT | TT | CC | CT | TT | CC | CT | TT |
| No. of patients | 20 | 25 | 9 | 12 | 9 | 7 | 32 | 34 | 16 |
| LS means | 47.6 | 54.9 | 68.4 | 45.5 | 56.8 | 50.4 | 47.8 | 54.4 | 58.9 |
| P-value | 0.0164 | 0.0164 | 0.0164 | 0.0819 | 0.0819 | 0.0819 | 0.0214 | 0.0214 | 0.0214 |

Figure 4:
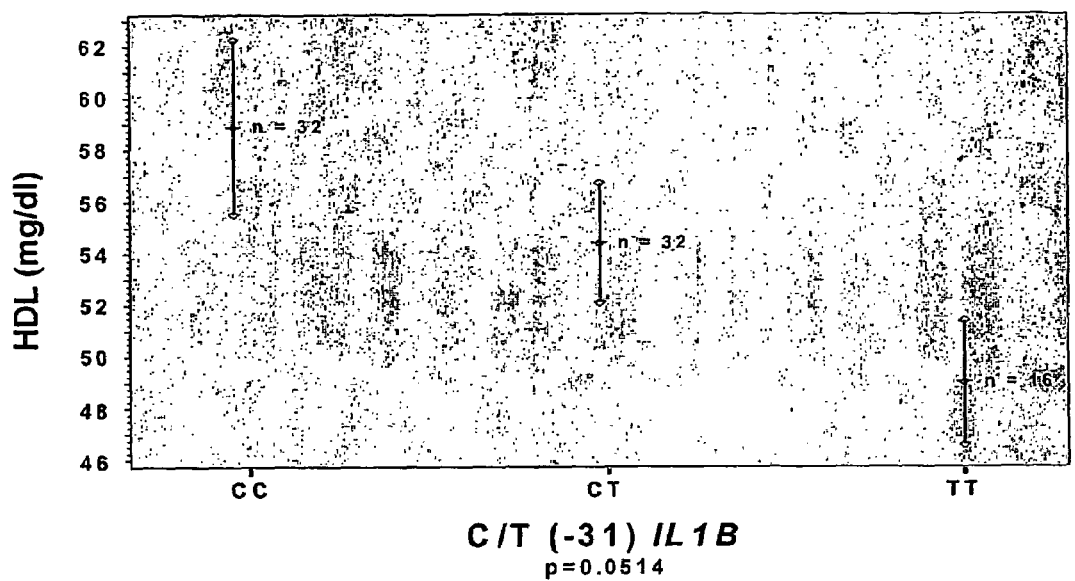
FIG. 4: LS mean HDL cholesterol levels compared to the (-31) IL-1β CC, CT or TT genotypes in all treatment groups combined within the RAD B251 clinical trial.

It has been previously reported that the IL-1β (-511) polymorphism is in strong linkage disequilibrium to another polymorphism in the IL-1β promoter at position (-31). See El-Omar et al., Nature, Vol. 404, pp. 398-402 (2000). In this study, 254 alleles were tested in patients consenting to pharmacogenetic analysis in the RAD B251 clinical trial. It is reported that the IL-1β (-511) and (-31) polymorphisms are in 99.2% linkage disequilibrium. Therefore, a similar association would occur with the IL-1β (-511) polymorphism and cholesterol levels could be detected as with the IL-1β (-31) polymorphism. Statistical analysis of the RAD B251 clinical data set to the IL-1β (-31) polymorphism identified a significant association with cholesterol levels. As shown in Table 5 and FIG. 2, the IL-1β (-31) (C-C) genotype in patients from both treatment groups together correlated with the highest increase in levels of total cholesterol measured at their last visit (p=0.0013). To analyze this correlation further, it was tested whether an association existed between the IL-1β (-31) genotype and levels of HDL and LDL. As shown in FIG. 4 and Table 7, the IL-1β (-31) (C-C) genotype in patients from both treatment groups together weakly correlated with the highest levels of HDL measured at their last visit (p=0.0514).

TABLE 7

LS Mean HDL Levels (mg/dL) by (−31) IL-1β CC, CT or TT Genotypes and Treatment Groups Within the RAD B251 Clinical Trial

|  | RAD (1.5 and 3.0 mg/day) | | | MMF (2 mg/day) | | | RAD and MMF treatment groups combined | | |
|---|---|---|---|---|---|---|---|---|---|
| Genotype | CC | CT | TT | CC | CT | TT | CC | CT | TT |
| No. of patients | 9 | 26 | 19 | 7 | 9 | 12 | 16 | 35 | 31 |
| LS means | 65.1 | 55 | 48.4 | 50.4 | 56.8 | 45.5 | 58.9 | 54.4 | 47.8 |
| P-value | 0.0205 | 0.0205 | 0.0205 | 0.1893 | 0.1893 | 0.1893 | 0.0514 | 0.0514 | 0.0514 |

Figure 5:
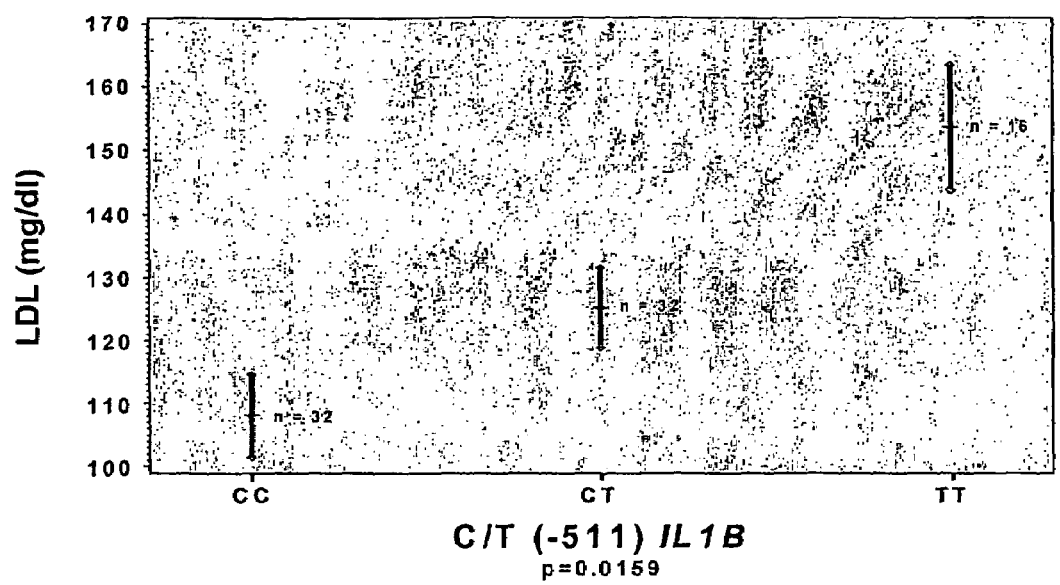
FIG. 5: LS mean LDL cholesterol levels compared to the (-511) IL-1β CC, CT or TT genotypes in all treatment groups within the RAD B251 clinical trial.

A similar correlation was identified with LDL levels as well (p=0.0159, FIG. 5 and Table 8).

TABLE 8

LS Mean LDL Levels (mg/dL) by (−511) IL-1β CC, CT or TT Genotypes and Treatment Groups Within the RAD B251 Clinical Trial

|  | RAD (1.5 and 3.0 mg/day) | | | MMF (2 mg/day) | | | RAD and MMF treatment groups combined | | |
|---|---|---|---|---|---|---|---|---|---|
| Genotype | CC | CT | TT | CC | CT | TT | CC | CT | TT |
| No. of patients | 20 | 25 | 9 | 12 | 9 | 7 | 32 | 34 | 16 |
| LS means | 112.5 | 123.6 | 144.5 | 113.9 | 118.6 | 143.7 | 110.5 | 123.8 | 145.8 |
| P-value | 0.1646 | 0.1646 | 0.1646 | 0.2848 | 0.2848 | 0.2848 | 0.0159 | 0.0159 | 0.0159 |

Figure 6:
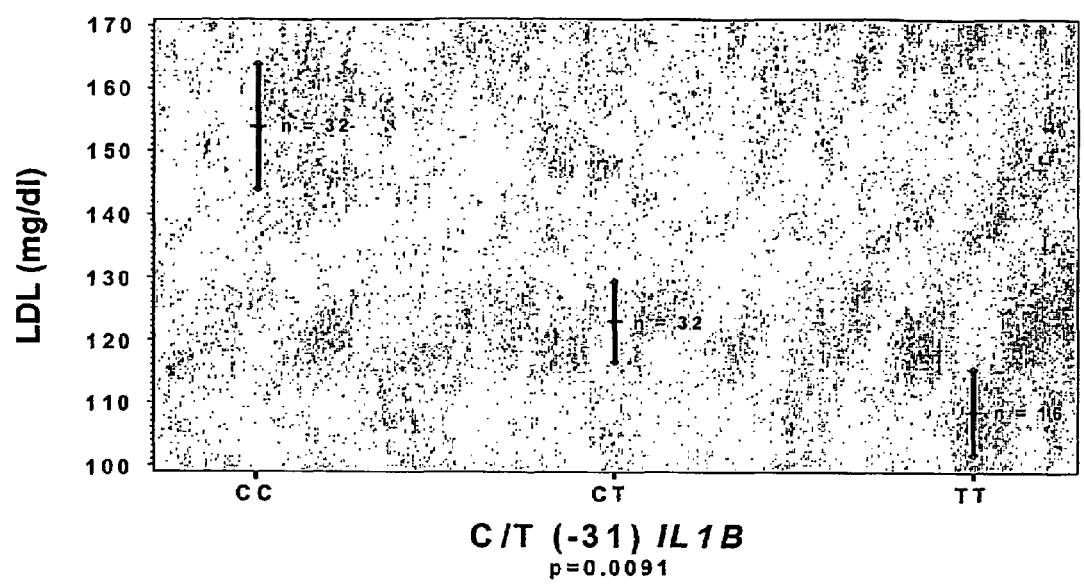
FIG. 6: LS mean LDL cholesterol levels compared to the (-31) IL-1β CC, CT or TT genotypes in all treatments groups within the RAD B251 clinical trial.
Figure 7:
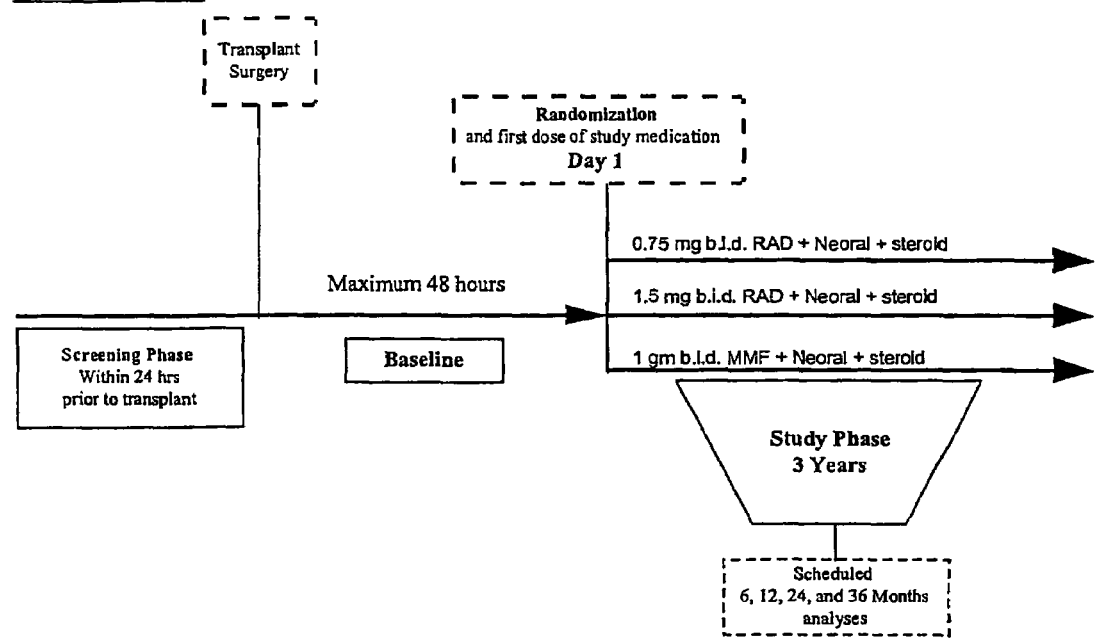
FIG. 7: Study Schematic for the RAD B251 clinical trial.

A stronger correlation was identified with LDL levels and the -31 IL-1β polymorphism (p=0.0091, FIG. 6 and Table 9).

TABLE 9

LS Mean LDL Levels (mg/dL) by (−31) IL-1β CC, CT or TT Genotypes and Treatment Groups Within the RAD B251 Clinical Trial

| Genotype | RAD (1.5 and 3.0 mg/day) | | | MMF (2 mg/day) | | | RAD and MMF treatment groups combined | | |
|---|---|---|---|---|---|---|---|---|---|
| | CC | CT | TT | CC | CT | TT | CC | CT | TT |
| No. of patients | 9 | 26 | 19 | 7 | 9 | 12 | 16 | 35 | 31 |
| LS means | 145.1 | 124.1 | 112.2 | 143.1 | 119.8 | 107.8 | 145.9 | 124.5 | 108.5 |
| P-value | 0.143 | 0.143 | 0.143 | 0.2061 | 0.2061 | 0.2061 | 0.0091 | 0.0091 | 0.0091 |

Importantly, the HDL to LDL ratios remained unchanged between genotype groups. The findings presented in this study would predict a greater likelihood of individuals with a certain allele to experience persistent increases in cholesterol levels upon treatment with the RAD/NEORAL® regimen than individuals that do not possess the allele. A similar trend was identified in individuals treated with the MMF/NEORAL® regimen, but the results did not meet the p=0.05 statistical significance.

Since total blood cholesterol levels ≧240 mg/dL are generally considered to be excessively elevated, it was therefore decided to determine the odds ratio for a patient with the IL-1β (-511) or IL-1β (-31) polymorphisms to encounter an increase in total blood cholesterol levels resulting in a final concentration ≧240 mg/dL after being treated with the RAD/NEORAL® or MMF/NEORAL® regimens. See, *Cecil Textbook of Medicine*, Goldman and Bennett, editors, Saunders, 6$^{th}$ Edition (2000).

As shown in Table 10 below, the odds ratio indicates that patients are 5.67 (95% confidence limits: 1.20-9.01) times more likely to have an increase in total blood cholesterol levels to a final concentration ≧240 mg/dL when treated with the RAD/NEORAL® regimen if they contain a T at position (-511) in the IL-1β gene promoter, or 7.23 (95% confidence limits: 1.20-9.01) times more likely to have an increase in total blood cholesterol levels to a final concentration ≧240 mg/dL when treated with the RAD/NEORAL® regimen if they contain a C at position (-31) in the IL-1β gene promoter. These findings are statistically significant (p=0.0207 and p=0.0096, respectively) and could be used as a precautionary measure in the treatment of transplantation patients with the RAD/NEORAL® regimen since hypercholesterolemia is easily treatable.

TABLE 10

Odds Ratio for the (−511) and (−31) IL-1β Genotypes and Cholesterol Levels

| | (−511) IL-1β Polymorphism | | |
|---|---|---|---|
| Obs. | Genotype | | |
| Exp. | CT-TT | CC | Total |
| >239 mg/dL | 24 | 7 | 31 |
| | 18.90 | 12.10 | |
| ≦239 mg/dL | 26 | 25 | 51 |
| | 31.10 | 19.90 | |
| | 50 | 32 | 82 |

Odds ratio = 5.67 (95% CI: 1.20-9.01)
p = 0.0207 (Fisher's Exact test)

| | (−31) IL-1β Polymorphism | | |
|---|---|---|---|
| Obs. | Genotype | | |
| Exp. | CC-CT | TT | Total |
| >239 mg/dL | 25 | 6 | 31 |
| | 19.28 | 11.72 | |
| ≦239 mg/dL | 26 | 25 | 51 |
| | 31.72 | 19.28 | |
| | 51 | 31 | 82 |

Odds ratio = 7.23 (95% CI: 1.20-9.01)
p = 0.0096 (Fisher's Exact test)

Bonferroni Correction for Multiple Testing

A correction factor is needed due to the number of SNPs that were analyzed in this study. To do so, the Bonferroni correction method was performed which dictated a p-value of 0.0019.

$$\text{Bonferroni} = \frac{0.05}{\eta} = \frac{0.05}{26} = 0.0019$$

$\eta$ = RAD_number_of_tests

Therefore, the finding between the IL-1β (-511) and IL-1β (-31) polymorphisms and total cholesterol levels (p=0.0018 and p=0.0013, respectively) is still be considered as significant.

Linkage disequilibrium of the (-511) and (-31) IL-1β SNPs

It has been reported that the IL-1β (-511) C→T polymorphism is in strong linkage disequilibrium (99.5%) with another polymorphism within the IL-1β promoter located at position (-31) that results in a T→C base transition. See El-Omar et al., *Nature*, Vol. 404, pp. 398-402 (2000). Therefore, it is predicted that patients with a T at position (-511) of the IL-1β promoter would have a C at position (-31). This finding is confirmed in the patients tested in these two trials. In the wild-type IL-1β gene, T is found at position at -31. This T is very important for the expression of IL-1β because it is part of the TATA box sequence (TATAAAA) which plays a critical role in the transcriptional initiation of IL-1β. In general, TATA box sequences are involved in recruiting and positioning the transcriptional machinery at the correct position within genes to ensure that transcription begins at the correct place. The T→C polymorphism at position (-31) would disrupt this important TATA box sequence (TATAAAA to CATAAAA), thus making it inactive and prohibiting the efficient initiation of transcription of the IL-1β gene. The lack of binding of the transcriptional machinery to this altered IL-1β TATA box sequence has been shown. See El-Omar, supra.

Therefore, the existence of any other polymorphism which is in linkage disequilibrium with either the polymorphism within the IL-1β promoter (located at position (-31) that results in a T→C base transition) or the polymorphism located at -511 (C→T) of the IL-1β promoter, would also have a predictive effect on the degree of cholesterol elevation expected in a patient during treatment with an IM. The means for the determination of other polymorphisms which are in linkage disequilibrium with the (-31) polymorphism is well known to one of skill in the art. Any such polymorphism, now known or discovered in the future, could be used in the methods of this invention to predict the degree of likely cholesterol elevation in patients treated with an IM or to help determine treatment choices for such patients.

Biological Significance of the Findings

The IL-1β (-31) (C-C) genotype has clinical relevance. IL-1β has been shown to inhibit cholesterol biosynthesis by 25%. See El-Omar et al., supra. Therefore, the result of this polymorphism would mean that patients with the IL-1β (-31) (C-C) genotype, corresponding to the IL-1β (-511) (T-T) genotype, would have decreased levels of IL-1β, thereby losing the inhibition of cholesterol biosynthesis by IL-1β, resulting in elevated levels of cholesterol in the blood. This type of finding was observed in the RAD B251 trial. As shown in Tables 4 and 5 and FIGS. 1-2, patients with the IL-1β (-511) (T-T) genotype and IL-1β (-31) (C-C) genotype had the highest least square mean levels of total cholesterol, regardless of treatment.

It has also been reported that IL-1β increases LDL receptor gene expression through the activation of the extracellular signal-regulated kinases (ERKs). See Kumar et al., *J. Biol. Chem.*, Vol. 273, pp. 15742-15748 (1998).

Elevations in LDL receptor expression would result in an increase in the amount of cholesterol that is internalized into cells, thereby lowering total cholesterol levels in the blood. This has relevance to RAD (everolimus) since this drug has been shown to inhibit biochemical pathways that are required for cell progression through late G1 and entry into S. Importantly, the ERKs have been shown to be involved in this process. Therefore, it is possible that ERK activity would be decreased by everolimus. Because everolimus would inhibit ERK activity, LDL receptor expression would decrease in all patients, independently of IL-1β expression, thereby causing increased levels of LDL and thus total cholesterol in patients taking everolimus. It is unlikely that everolimus completely inhibits ERK activation. Therefore, patients with the IL-1β (-511) (T-T) and IL-1β (-31) (C-C) genotypes would be able induce some expression of the LDL receptor. However, those patients would have very low levels of IL-1β, and therefore less LDL receptor expression, thereby resulting in lower amounts of cholesterol being internalized into cells and elevating blood cholesterol levels. This explanation would thus account for the highest levels of cholesterol observed in patients with the IL-1β (-31) (C-C) genotype. Significantly, patients with the IL-1β (-511) (T-T) genotype, corresponding to the IL-1β (-31) (C-C) genotype, had the significantly higher levels of LDL (p=0.0159) as compared to patients with other IL-1β genotypes (FIG. 3 and Table 4).

Identification and Characterization of SNPs

Many different techniques can be used to identify and characterize SNPs, including single-strand conformation polymorphism analysis, heteroduplex analysis by denaturing high-performance liquid chromatography (DHPLC), direct DNA sequencing and computational methods. See Shi, *Clin. Chem.*, Vol. 47, pp. 164-172 (2001). Thanks to the wealth of sequence information in public databases, computational tools can be used to identify SNPs in silico by aligning independently submitted sequences for a given gene (either cDNA or genomic sequences). Comparison of SNPs obtained experimentally and by in silico methods showed that 55% of candidate SNPs found by SNPFinder (http://lpgws.nci.nih.gov:82/perl/snp/snp_cgi.pl) have also been discovered experimentally. See, Cox et al., *Hum. Mutal.*, Vol. 17, pp. 141-150 (2001). However, these in silico methods could only find 27% of true SNPs.

The most common SNP typing methods currently include hybridization, primer extension and cleavage methods. Each of these methods must be connected to an appropriate detection system. Detection technologies include fluorescent polarization, (see Chan et al., *Genome Res.*, Vol. 9, pp. 492-499 (1999)), luminometric detection of pyrophosphate release (pyrosequencing), (see Ahmadiian et al., *Anal. Biochem.*, Vol. 280, pp. 103-110 (2000)), fluorescence resonance energy transfer (FRET)-based cleavage assays, DHPLC, and mass spectrometry (see Shi, *Clin. Chem.*, Vol. 47, pp. 164-172 (2001) and U.S. Pat. No. 6,300,076 B1). Other methods of detecting and characterizing SNPs are those disclosed in U.S. Pat. Nos. 6,297,018 B1 and 6,300,063 B1. The disclosures of the above references are incorporated herein by reference in their entirety.

In a particularly preferred embodiment the detection of the polymorphism can be accomplished by means of so called INVADER™ technology (available from Third Wave Technologies Inc. Madison, Wis.). In this assay, a specific upstream "invader" oligonucleotide and a partially overlapping downstream probe together form a specific structure when bound to complementary DNA template. This structure is recognized and cut at a specific site by the Cleavase enzyme, and this results in the release of the 5' flap of the probe oligonucleotide. This fragment then serves as the "invader" oligonucleotide with respect to synthetic secondary targets and secondary fluorescently-labeled signal probes contained in the reaction mixture. This results in specific cleavage of the secondary signal probes by the Cleavase enzyme. Fluorescence signal is generated when this secondary probe, labeled with dye molecules capable of fluorescence resonance energy transfer, is cleaved. Cleavases have stringent requirements relative to the structure formed by the overlapping DNA sequences or flaps and can, therefore, be used to specifically detect single base pair mismatches immediately upstream of the cleavage site on the downstream DNA strand. See Ryan et al., *Molecular Diagnosis*, Vol. 4, No 2, pp. 135-144 (1999); and Lyamichev et al., *Nat Biotechnol.*, Vol. 17, pp. 292-296 (1999); see also U.S. Pat. Nos. 5,846,717 and 6,001,567 (the disclosures of which are incorporated herein by reference in their entirety).

In some embodiments, a composition contains two or more differently labeled genotyping oligonucleotides for simultaneously probing the identity of nucleotides at two or more polymorphic sites. It is also contemplated that primer compositions may contain two or more sets of allele-specific primer pairs to allow simultaneous targeting and amplification of two or more regions containing a polymorphic site.

IL-1β genotyping oligonucleotides of the invention may also be immobilized on or synthesized on a solid surface such as a microchip, bead or glass slide (see, e.g., WO 98/20020 and WO 98/20019). Such immobilized genotyping oligonucleotides may be used in a variety of polymorphism detection assays, including but not limited to probe hybridization and polymerase extension assays. Immobilized IL-1β genotyping oligonucleotides of the invention may comprise an ordered array of oligonucleotides designed to rapidly screen a DNA sample for polymorphisms in multiple genes at the same time.

An allele-specific oligonucleotide primer of the invention has a 3' terminal nucleotide, or preferably a 3' penultimate nucleotide, that is complementary to only one nucleotide of a particular SNP, thereby acting as a primer for polymerase-mediated extension only if the allele containing that nucleotide is present. Allele-specific oligonucleotide primers hybridizing to either the coding or noncoding strand are contemplated by the invention. An ASO primer for detecting IL-1β gene polymorphisms could be developed using techniques known to those of skill in the art.

Other genotyping oligonucleotides of the invention hybridize to a target region located one to several nucleotides downstream of one of the novel polymorphic sites identified herein. Such oligonucleotides are useful in polymerase-mediated primer extension methods for detecting one of the novel polymorphisms described herein and therefore such genotyping oligonucleotides are referred to herein as "primer-extension oligonucleotides". In a preferred embodiment, the 3'-terminus of a primer-extension oligonucleotide is a deoxynucleotide complementary to the nucleotide located immediately adjacent to the polymorphic site.

In another embodiment, the invention provides a kit comprising at least two genotyping oligonucleotides packaged in separate containers. The kit may also contain other components, such as hybridization buffer (where the oligonucleotides are to be used as a probe) packaged in a separate container. Alternatively, where the oligonucleotides are to be used to amplify a target region, the kit may contain, packaged in separate containers, a polymerase and a reaction buffer optimized for primer extension mediated by the polymerase, such as PCR. The above described oligonucleotide compositions and kits are useful in methods for genotyping and/or haplotyping the IL-1β gene in an individual.

As used herein, the term "haplotype with regard to the IL-1β gene" shall refer to the haplotype consisting of the combination of the polymorphisms at the -511 and the -31 position of the IL-1β gene and these haplotypes shall be named in the following manner; the haplotype shall be called "high cholesterol" if both the C to T polymorphism at the polymorphic site -511 of the IL-1β gene (position 1423 of sequence X04500, which is incorporated by reference and is SEQ ID NO:11 of the sequence listing) and the T to C polymorphism at the polymorphic site - 31 of the IL-1β gene (position 1903 of sequence X04500, which is incorporated by reference and is SEQ ID NO:11 of the sequence listing) are present in one copy of the IL-1β gene. Conversely, the haplotype shall be called "low cholesterol" if both these polymorphisms are not present in a given copy of the IL-1β gene and therefore the nucleotide at site -31 of this IL-1β gene is a T and the nucleotide at site -511 is a C in this IL-1β gene in the chromosome referred to.

One embodiment of the genotyping method involves isolating from the individual a nucleic acid mixture comprising the two copies of the IL-1β gene, or a fragment thereof, that are present in the individual, and determining the identity of the nucleotide pair at one or more of the polymorphic sites in the two copies to assign a IL-1β genotype to the individual. As will be readily understood by the skilled artisan, the two "copies" of a gene in an individual may be the same allele or may be different alleles. In a particularly preferred embodiment, the genotyping method comprises determining the identity of the nucleotide pair at each polymorphic site.

Typically, the nucleic acid mixture or protein is isolated from a biological sample taken from the individual, such as a blood sample or tissue sample. Suitable tissue samples include whole blood, semen, saliva, tears, urine, fecal material, sweat, buccal smears, skin, and biopsies of specific organ tissues, such as muscle or nerve tissue and hair. The nucleic acid mixture may be comprised of genomic DNA, messenger polyribonucleotide (mRNA), or cDNA and, in the latter two cases, the biological sample must be obtained from an organ in which the IL-1β gene is expressed. Furthermore it will be understood by the skilled artisan that mRNA or cDNA preparations would not be used to detect polymorphisms located in introns, in 5' and 3' non-transcribed regions or in promoter regions. If an IL-1 gene fragment is isolated, it must contain the polymorphic site(s) to be genotyped.

One embodiment of the haplotyping method comprises isolating from the individual a nucleic acid molecule containing only one of the two copies of the IL-1β gene, or a fragment thereof, that is present in the individual and determining in that copy the identity of the nucleotide at one or more of the polymorphic sites in that copy to assign a IL-1β haplotype to the individual. The nucleic acid may be isolated using any method capable of separating the two copies of the IL-1β gene or fragment, including but not limited to, one of the methods described above for preparing IL-1β isogenes, with targeted in vivo cloning being the preferred approach.

As will be readily appreciated by those skilled in the art, any individual clone will only provide haplotype information on one of the two IL-1β gene copies present in an individual. If haplotype information is desired for the individuals other copy, additional IL-1β clones will need to be examined. Typically, at least five clones should be examined to have more than a 90% probability of haplotyping both copies of the IL-1β gene in an individual. In a particularly preferred embodiment, the nucleotide at each of polymorphic site is identified.

In a preferred embodiment, a IL-1β haplotype pair is determined for an individual by identifying the phased sequence of nucleotides at one or more of the polymorphic sites in each copy of the IL-1β gene that is present in the individual. In a particularly preferred embodiment, the haplotyping method comprises identifying the phased sequence of nucleotides at each polymorphic site in each copy of the IL-1β gene. When haplotyping both copies of the gene, the identifying step is preferably performed with each copy of the gene being placed in separate containers. However, it is also envisioned that if the two copies are labeled with different tags, or are otherwise separately distinguishable or identifiable, it could be possible in some cases to perform the method in the same container. For example, if first and second copies of the gene are labeled with different first and second fluorescent dyes, respectively, and an allele-specific oligonucleotide labeled with yet a third different fluorescent dye is used to assay the polymorphic site(s), then detecting a combination of the first and third dyes would identify the polymorphism in the first gene copy while detecting a combination of the second and third dyes would identify the polymorphism in the second gene copy.

In both the genotyping and haplotyping methods, the identity of a nucleotide (or nucleotide pair) at a polymorphic site(s) may be determined by amplifying a target region(s) containing the polymorphic site(s) directly from one or both copies of the IL-1β gene, or fragment thereof, and the sequence of the amplified region(s) determined by conventional methods. It will be readily appreciated by the skilled artisan that the same nucleotide will be detected twice at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for all individual homozygous at that site, or both guanine and cytosine, if the individual is heterozygous at that site. Alternatively, the site may be negatively determined to be not guanine (and thus cytosine/cytosine) or not cytosine (and thus guanine/guanine).

In addition, the identity of the allele(s) present at any of the novel polymorphic sites described herein may be indirectly determined by genotyping a polymorphic site not disclosed herein that is in linkage disequilibrium with the polymorphic site that is of interest. Two sites are said to be in linkage disequilibrium if the presence of a particular variant at one site enhances the predictability of another variant at the second site. See Stevens, *Mol. Diag.*, Vol. 4, pp. 309-317 (1999). Polymorphic sites in linkage disequilibrium with the presently disclosed polymorphic sites may be located in regions of the gene or in other genomic regions not examined herein. Genotyping of a polymorphic site in linkage disequilibrium with the novel polymorphic sites described herein may be performed by, but is not limited to, any of the above-mentioned methods for detecting the identity of the allele at a polymorphic site.

The target region(s) may be amplified using any oligonucleotide-directed amplification method, including but not limited to polymerase chain reaction (PCR) (U.S. Pat. No. 4,965,188), ligase chain reaction (LCR) (see Barany et al., *Proc. Natl. Acad. Sci. USA*, Vol. 88, pp. 189-193 (1991); and WO 90/01069), and oligonucleotide ligation assay (OLA) (see Landegren et al., *Science*, Vol. 241, pp. 1077-1080 (1988)). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20-25 nucleotides long. The exact length of the oligonucleotide will depend on many factors that are routinely considered and practiced by the skilled artisan.

Other known nucleic acid amplification procedures may be used to amplify the target region including transcription-based amplification systems (see U.S. Pat. Nos. 5,130,238 and 5,169,766; EP 329,822; and WO 89/06700) and isothermal methods. See Walker et al., *Proc. Natl. Acad. Sci. USA*, Vol. 89, pp. 392-396 (1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs. Preferably, the members of the set have melting temperatures within 5° C. and more preferably within 2° C., of each other when hybridizing to each of the polymorphic sites being detected.

Hybridization of an allele-specific oligonucleotide to a target polynucleotide may be performed with both entities in solution or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes and beads. The solid support may be treated, coated or derivatized to facilitate the immobilization of the allele-specific oligonucleotide or target nucleic acid.

The genotype or haplotype for the IL-1β gene of an individual may also be determined by hybridization of a nucleic sample containing one or both copies of the gene to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (see Winter et al., *Proc. Natl. Acad. Sci. USA*, Vol. 82, p. 7575 (1985); and Meyers et al., *Science*, Vol. 230, p. 1242 (1985)) and proteins which recognize nucleotide mismatches, such as the *E. coli* mutS protein. See Modrich, *Ann. Rev. Genet*, Vol. 25, pp. 229-253 (1991). Alternatively, variant alleles can be identified by single strand conformation polymorphism (SSCP) analysis (see Orita et al., Genomics, Vol. 5, pp. 874-879 (1989); and Humphries et al., *Molecular Diagnosis of Genetic Diseases*, Elles, Ed., pp. 321-340 (1996)) or denaturing gradient gel electrophoresis (DGGE). See Wartell et at., *Nucl. Acids Res.*, Vol. 18, pp. 2699-2706 (1990); and Sheffield et al., *Proc. Natl. Acad. Sci. USA*, Vol. 86, pp. 232-236 (1989).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524). Related methods are disclosed in WO 91/02087, WO 90/09455, WO 95/17676, U.S. Pat. Nos. 5,302,509 and 5,945,283. Extended primers containing a polymorphism may be detected by mass spectrometry as described in U.S. Pat. No. 5,605,798. Another primer extension method is allele-specific PCR. See Ruaflo et al., Nucl. Acids Res., Vol. 17, p. 8392 (1989); Ruafio et al., *Nucl. Acids Res.*, Vol. 19, pp. 6877-6882 (1991); WO 93/22456; and Turki et al., *J. Clin. Invest*, Vol. 95, pp. 1635-1641 (1995). In addition, multiple polymorphic sites may be investigated by simultaneously amplifying multiple regions of the nucleic acid using sets of allel-specific primers as described in Wallace et al. (WO 89/10414).

In a preferred embodiment, the haplotype frequency data for each ethnogeographic group is examined to determine whether it is consistent with Hardy-Weinberg equilibrium. Hardy-Weinberg equilibrium (see Hartl et al., *Principles of Population Genomics*, Sinauer Associates, 3$^{rd}$ Edition, Sunderland, Mass. (1997), postulates that the frequency of finding the haplotype pair $H_1/H_2$ is equal to $P_{H\text{-}W}(H_1/H_2)=2p(H_1)$ $p(H_2)$ if $H_1 \ne H_2$ and $P_{H\text{-}W}(H_1/H_2)=p(H_1)p(H_2)$ if $H_1=H_2$. A statistically significant difference between the observed and expected haplotype frequencies could be due to one or more factors including significant inbreeding in the population group, strong selective pressure on the gene, sampling bias, and/or errors in the genotyping process. If large deviations from Hardy-Weinberg equilibrium are observed in an ethnogeographic group, the number of individuals in that group can be increased to see if the deviation is due to a sampling bias. If a larger sample size does not reduce the difference between observed and expected haplotype pair frequencies, then one may wish to consider haplotyping the individual using a direct haplotyping method such as, for example, CLASPER System™ technology (U.S. Pat. No. 5,866,404), SMD or allele-specific long-range PCR. See Michalotos-Beloin et al., *Nucl. Acids Res.*, Vol. 24, pp. 4841-4843 (1996).

In one embodiment of this method for predicting an IL-1β haplotype pair, the assigning step involves performing the following analysis. First, each of the possible haplotype pairs is compared to the haplotype pairs in the reference population. Generally, only one of the haplotype pairs in the reference population matches a possible haplotype pair and that pair is assigned to the individual. Occasionally, only one haplotype represented in the reference haplotype pairs is consistent with a possible haplotype pair for an individual, and in such cases the individual is assigned a haplotype pair containing this known haplotype and a new haplotype derived by subtracting the known haplotype from the possible haplotype pair. In rare cases, either no haplotype in the reference population are consistent with the possible haplotype pairs, or alternatively, multiple reference haplotype pairs are consistent with the possible haplotype pairs. In such cases, the individual is preferably haplotyped using a direct molecular haplotyping method such as, for example, CLASPER System™ technology (U.S. Pat. No. 5,866,404), SMD or allele-specific long-range PCR. See Michalotos-Beloin et al., supra.

GLOSSARY

Allele A particular form of a gene or DNA sequence at a specific chromosomal location (locus).

Antibodies Includes polyclonal and monoclonal antibodies, chimeric, single-chain, and humanized antibodies, as well as Fab fragments, including the products of an Fab or other immunoglobulin expression library.

Candidate gene A gene which is hypothesized to be responsible for a disease, condition, or the response to a treatment, or to be correlated with one of these.

Full-genotype The unphased 5' to 3' sequence of nucleotide pairs found at all known polymorphic sites in a locus on a pair of homologous chromosomes in a single individual.

Full-haplotype The 5' to 3' sequence of nucleotides found at all known polymorphic sites in a locus on a single chromosome from a single individual.

Gene A segment of DNA that contains all the information for the regulated biosynthesis of an RNA product, including promoters, exons, introns, and other untranslated regions that control expression.

Genotype An unphased 5' to 3' sequence of nucleotide pair(s) found at one or more polymorphic sites in a locus on a pair of homologous chromosomes in an individual. As used herein, genotype includes a full-genotype and/or a sub-genotype as described below.

Genotypinq A process for determining a genotype of an individual.

Haplotype A 5' to 3' sequence of nucleotides found at one or more linked polymorphic sites in a locus on a single chromosome from a single individual.

Haplotype data Information concerning one or more of the following for a specific gene: a listing of the haplotype pairs in each individual in a population; a listing of the different haplotypes in a population; frequency of each haplotype in that or other populations, and any known associations between one or more haplotypes and a trait.

Haplotype pair Two haplotypes found for a locus in a single individual.

Haplotyping A process for determining one or more haplotypes in an individual and includes use of family pedigrees, molecular techniques and/or statistical inference.

Homolog A generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog" and "paralog".

Identity A relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

Isoform A particular form of a gene, mRNA, cDNA or the protein encoded thereby, distinguished from other forms by its particular sequence and/or structure.

Isogene One of the isoforms of a gene found in a population. An isogene contains all of the polymorphisms present in the particular isoform of the gene.

Isolated As applied to a biological molecule, such as RNA, DNA, oligonucleotide or protein; isolated means the molecule is substantially free of other biological molecules, such as nucleic acids, proteins, lipids, carbohydrates, or other material, such as cellular debris and growth media. Generally, the term "isolated" is not intended to refer to a complete absence of such material or to absence of water, buffers, or salts, unless they are present in amounts that substantially interfere with the methods of the present invention.

Linkage Describes the tendency of genes to be inherited together as a result of their location on the same chromosome; measured by percent recombination between loci.

Linkage disequilibrium Describes a situation in which some combinations of genetic markers occur more or less frequently in the population than would be expected from their distance apart. It implies that a group of markers has been inherited coordinately. It can result from reduced recombination in the region or from a founder effect, in which there has been insufficient time to reach equilibrium since one of the markers was introduced into the population.

Locus A location on a chromosome or DNA molecule corresponding to a gene or a physical or phenotypic feature.

Modified bases Include, e.g., tritylated bases and unusual bases, such as inosine. A variety of modifications may be made to DNA and RNA; thus, polynucleotide embraces chemically, enzymatically or metabolically modified forms of polynucleotides as typically found in nature, as well as the chemical forms of DNA and RNA characteristic of viruses and cells. Polynucleotide also embraces relatively short polynucleotides, often referred to as oligonucleotides.

Naturally-occurring A term used to designate that the object it is applied to, e.g., naturally-occurring polynucleotide or polypeptide, can be isolated from a source in nature and which has not been intentionally modified by man.

Nucleotide pair The nucleotides found at a polymorphic site on the two copies of a chromosome from an individual.

Ortholog A polynucleotide or polypeptide that is the functional equivalent of the polynucleotide or polypeptide in another species.

Paralog A polynucleotide or polypeptide that within the same species which is functionally similar.

Phased As applied to a sequence of nucleotide pairs for two or more polymorphic sites in a locus, phased means the combination of nucleotides present at those polymorphic sites on a single copy of the locus is known.

Polymorphic site (PS) A position within a locus at which at least two alternative sequences are found in a population, the most frequent of which has a frequency of no more than 99%.

Polymorphic variant A gene, mRNA, cDNA, polypeptide or peptide whose nucleotide or amino acid sequence varies from a reference sequence due to the presence of a polymorphism in the gene.

Polymorphism Any sequence variant present at a frequency of >1% in a population. The sequence variation observed in an individual at a polymorphic site.

Polymorphisms include nucleotide substitutions, insertions, deletions and microsatellites and may, but need not, result in detectable differences in gene expression or protein function.

Polymorphism data Information concerning one or more of the following for a specific gene: location of polymorphic sites; sequence variation at those sites; frequency of polymorphisms in one or more populations; the different genotypes and/or haplotypes determined for the gene; frequency of one or more of these genotypes and/or haplotypes in one or more populations; any known association(s) between a trait and a genotype or a haplotype for the gene.

Polymorphism database A collection of polymorphism data arranged in a systematic or methodical way and capable of being individually accessed by electronic or other means.

Polynucleotide Any RNA or DNA, which may be unmodified or modified RNA or DNA. Polynucleotides include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

Polypeptide Any polypeptide comprising two or more amino acids joined to each other by peptide bonds or modified peptide bonds, i.e., peptide isosteres. Polypeptide refers to both short chains, commonly referred to as peptides, oligopeptdes or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

Population group A group of individuals sharing a common characteristic, such as ethnogeographic origin, medical condition, response to treatment etc.

Reference population A group of subjects or individuals who are predicted to be representative of one or more characteristics of the population group. Typically, the reference population represents the genetic variation in the population at a certainty level of at least 85%, preferably at least 90%, more preferably at least 95% and even more preferably at least 99%.

Single Nucleotide Polymorphism (SNP) The occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bp from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

Splice variant cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of which may encode different amino acid sequences. The term "splice variant"also refers to the proteins encoded by the above cDNA molecules.

Sub-genotype The unphased 5' to 3'-sequence of nucleotides seen at a subset of the known polymorphic sites in a locus on a pair of homologous chromosomes in a single individual.

Sub-haplotype The 5' to 3' sequence of nucleotides seen at a subset of the known polymorphic sites in a locus on a single chromosome from a single individual.

Subject A human individual whose genotypes or haplotypes or response to treatment or disease state are to be determined.

Treatment A stimulus administered internally or externally to a subject.

Unphased As applied to a sequence of nucleotide pairs for two or more polymorphic sites in a locus, unphased means the combination of nucleotides present at those polymorphic sites on a single copy of the locus is not known.

See also, Human Molecular Genetics, $2^{nd}$ edition. Tom Strachan and Andrew P. Read. John Wiley and Sons, Inc. Publication, New York,

REFERENCES CITED

All references cited herein are incorporated herein by reference in their entirety and for all purposes to the same extent as if each individual publication or patent or patent application was specifically and individually indicated to be incorporated by reference in its entirety for all purposes. The discussion of references herein is intended merely to summarise the assertions made by their authors and no admission is made that any reference constitutes prior art. Applicants reserve the right to challenge the accuracy and pertinence of the cited references.

In addition, all GenBank accession numbers, Unigene Cluster numbers and protein accession numbers cited herein are incorporated herein by reference in their entirety and for all purposes to the same extent as if each such number was specifically and individually indicated to be incorporated by reference in its entirety for all purposes.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

We claim:

1. A method of determining predisposition to serum cholesterol elevation of greater than 239 mg/dL in a human patient upon treatment with everolimus comprising:

a) assaying a blood sample from the patient for the presence of a cytosine (C) at polymorphic site -31 of the IL-1β gene, which is position 1903 of SEQ ID NO 11; and b) determining that the patient has a predisposition to serum cholesterol elevation of greater than 239 mg/dL upon treatment with everolimus by the presence of a C at the polymorphic site -31 of the human IL-β gene.

2. A method of treating a human patient with everolimus comprising:

a) assaying a blood sample from the patient for a thymine (T) or cytosine (C) at polymorphic site -31 of the human IL-1β gene, which is position 1903 of SEQ ID NO:11; and b) treating the patient with everolimus if the patient has a T for both alleles at the polymorphic site -31 of the human IL-1β gene or treating the patient with everolimus and an alternative treatment if the patient has a C allele at the polymorphic site -31 of the human IL-1β gene.

3. The method of claim 2, wherein the alternative treatment comprises a cholesterol lowering medication selected from the group consisting of a bile acid sequestrant, a fibric acid derivative, an HMG-CoA reductase inhibitor, and nicotinic add.

* * * * *